US008487131B2

(12) United States Patent
Pellecchia

(10) Patent No.: US 8,487,131 B2
(45) Date of Patent: *Jul. 16, 2013

(54) OPTICALLY PURE APOGOSSYPOL DERIVATIVE AS PAN-ACTIVE INHIBITOR OF ANTI-APOPTOTIC B-CELL LYMPHOMA/LEUKEMIA-2 (BCL-2)

(75) Inventor: Maurizio Pellecchia, San Diego, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 189 days.

This patent is subject to a terminal disclaimer.

(21) Appl. No.: 12/960,349

(22) Filed: Dec. 3, 2010

(65) Prior Publication Data

US 2012/0004311 A1  Jan. 5, 2012

Related U.S. Application Data

(63) Continuation-in-part of application No. 12/760,380, filed on Apr. 14, 2010, now Pat. No. 8,039,668.

(60) Provisional application No. 61/169,686, filed on Apr. 15, 2009, provisional application No. 61/254,172, filed on Oct. 22, 2009.

(51) Int. Cl.
*C07C 233/65* (2006.01)
*A61K 31/16* (2006.01)

(52) U.S. Cl.
USPC .......................................... 564/156; 514/616

(58) Field of Classification Search
USPC ........................................ 564/156; 514/616
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 7,223,395 B2 | 5/2007 | Muller et al. | |
| 8,039,668 B2 * | 10/2011 | Pellecchia | 564/156 |
| 2004/0214902 A1 | 10/2004 | Wang et al. | |
| 2005/0027000 A1 | 2/2005 | Reed et al. | |
| 2006/0247305 A1 | 11/2006 | Wang et al. | |
| 2007/0037865 A1 | 2/2007 | Nunes et al. | |
| 2007/0149466 A1 | 6/2007 | Milburn et al. | |
| 2009/0105319 A1 | 4/2009 | Pellecchia et al. | |
| 2010/0267781 A1 | 10/2010 | Pellechia | |

FOREIGN PATENT DOCUMENTS

| | | |
|---|---|---|
| WO | WO 02/40966 A3 | 5/2002 |
| WO | WO 2005/009434 A2 | 2/2005 |

OTHER PUBLICATIONS

Carter et al., Chemotherapy of Cancer, second edition, John Wiley & Sons, N.Y., N.Y., 1981, pp. 362-365.*

Pettinelli and McFarlin, "Adoptive transfer of experimental allergic encephalomyelitis in SJL/J mice after in vitro activation of lymph node cells by myelin basic protein: requirement for Lyt 1+ 2- T lymphocytes", *J. Immunol.*, 127(4):1420-1423 (1981).

Rega et al., "Structure-based discovery of a new class of Bcl-xL antagonists", *Bioorg. Chem.*, 35(4):344-353 (2007).

White et al., "Antibody-targeted immunotherapy for treatment of malignancy", *Annu. Rev. Med.*, 52:125-145 (2001).

Yao et al., "Intra-articular injection of recombinant TRAIL induces synovial apoptosis and reduces inflammation in a rabbit knee model of arthritis", *Arthritis Res. Ther.*, 8(1): R16 pp. 1-8 (2006).

* cited by examiner

*Primary Examiner* — Shailendra Kumar
(74) *Attorney, Agent, or Firm* — Wilson, Sonsini, Goodrich & Rosati

(57) ABSTRACT

A compound of Formula I:

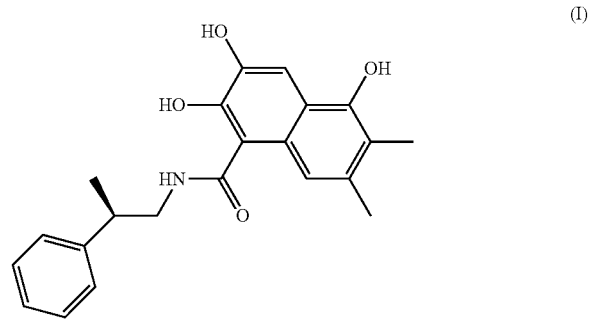

(I)

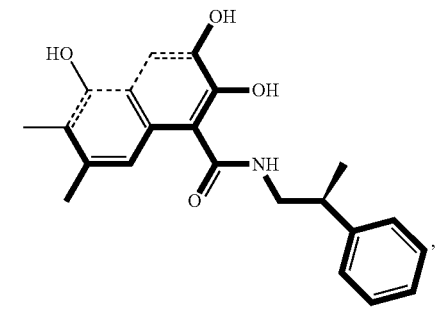

or a pharmaceutically acceptable salt thereof is disclosed. In addition, pharmaceutical compositions thereof, methods for preparing and methods for using this compound or composition for treating a variety of diseases, including cancer and inflammation are also provided.

16 Claims, 5 Drawing Sheets

OPTICALLY PURE APOGOSSYPOL DERIVATIVE AS PAN-ACTIVE INHIBITOR OF ANTI-APOPTOTIC B-CELL LYMPHOMA/LEUKEMIA-2 (BCL-2)

CROSS REFERENCE TO RELATED APPLICATIONS

This application is a continuation-in-part of U.S. patent application Ser. No. 12/760,380 filed Apr. 14, 2010, now U.S. Pat. No. 8,039,668, which claims the benefit of priority under 35 U.S.C. §119(e) to U.S. Provisional Application No. 61/254,172 filed on Oct. 22, 2009, and to U.S. Provisional Application No. 61/169,686, filed on Apr. 15, 2009, the disclosure of each of which is hereby incorporated by reference in their entirety for all purposes.

GRANT INFORMATION

This invention was made in part with government support under NIH (Grant U01 AI061139 and Grant CA113318), and CSRA (Grant No. 08-02). The United States Government has certain rights in this invention.

FIELD OF THE DISCLOSURE

The disclosure relates generally to a class of compounds derived from naphthalene, such as apogossypol and derivatives thereof, for treating a variety of disorders, diseases and pathologic conditions, and more specifically, for treating cancer, autoimmune diseases, and/or inflammation.

BACKGROUND OF THE DISCLOSURE

The apoptotic cascade in cells is known to lead to cell death. When anti-apoptotic proteins, such as BCL-2 family proteins, are overproduced by the cells, uncontrollable cell growth may ensue, potentially leading to the development of various serious diseases, disorders, and pathologies, particularly cancer. Programmed cell-death (apoptosis) plays critical roles in the maintenance of normal tissue homeostasis, ensuring a proper balance of cell production and cell loss. Defects in the regulation of programmed cell death promote tumorgenesis, and also contribute significantly to chemoresistance. Bcl-2 (B-cell lymphoma/leukemia-2) family proteins are central regulators of apoptosis. In humans, six anti-apoptotic members of the Bcl-2 family have been identified and characterized thus far, including Bcl-2, Bcl-$X_L$, Mcl-1, Bfl-1, Bcl-W and Bcl-B. Over-expression of anti-apoptotic Bcl-2 family proteins occurs in many human cancers and leukemias, and therefore these proteins are very attractive targets for the development of novel anticancer agents. Members of the Bcl-2 family proteins also include pro-apoptotic effectors such as Bak, Bax, Bad, Bim and Bid. Anti-apoptotic and pro-apoptotic Bcl-2 family proteins dimerize and negate each other's functions. Structural studies have elucidated a hydrophobic crevice on the surface of anti-apoptotic Bcl-2 family proteins that binds the BH3 dimerization domain of pro-apoptotic family members. Thus, molecules that mimic the BH3 domain of pro-apoptotic proteins induce apoptosis and/or abrogate the ability of anti-apoptotic Bcl-2 proteins to inhibit cancer cell death.

Apoptosis plays a role in tissue homeostatis, for the physiological removal of unwanted cells during development and in host defense mechanism. The BCL-2 family of proteins are believed to be involved in regulating of apoptosis. Specifically, members of the BCL-2 gene family can act to inhibit programmed cell death (e.g., BCL-2, BCL-$X_L$, ced-9) or promote cell death (e.g., Bax, Bak, BCL-$X_S$). Pro-survival members of this family, such as BCL-$X_L$, contain, on the surface, a hydrophobic groove in which is believed to allow binding of the BH3 domain of the pro-apoptotic counterpart. This binding is believed to play role in apoptosis regulation, in fact pro- and anti-survival proteins can reverse each other function through dimerization.

Therefore, a need exists to inhibit anti-apoptotic proteins, such as the BCL-2 family proteins. Various potential BCL-2 antagonists have been previously identified. However, none of these compounds inhibits all six proteins in the BCL-2 family, i.e., all of the following proteins: BCL-$X_L$, BCL-2, BCL-W, BCL-B, BFL-1, and MCL-1. For example, none of the previously identified synthetic BCL-2 antagonists was effective at inhibiting the protein BFL-1. Therefore, the efficiency of such antagonists is not as high as desired. In addition, the existing antagonists are characterized by other drawbacks, such as insufficiency or safety issues.

Defects in the regulation of programmed cell death may promote tumorgenesis, and also contribute to chemoresistance. Over-expression of anti-apoptotic BCL-2 family proteins occurs in many human cancers and leukemias, and therefore these proteins may be used as targets for the development of novel anticancer agents. Structural studies have elucidated a hydrophobic crevice on the surface of anti-apoptotic BCL-2 family proteins that binds the BH3 dimerization domain of pro-apoptotic family members. Thus, molecules that mimic the BH3 domain of pro-apoptotic proteins induce apoptosis and/or abrogate the ability of anti-apoptotic BCL-2 proteins to inhibit cancer cell death.

It has been previously shown that the natural product gossypol shown on FIG. 1A is an inhibitor of BCL-2, BCL-$X_L$ and MCL-1, functioning as a BH3 mimic. (−) Gossypol is currently in clinical trails, displaying single-agent antitumor activity in patients with advanced malignancies. Given that gossypol has toxicity problems likely due to two reactive aldehyde groups, we prepared apogossypol, a compound that lacks these aldehydes, but retains activity against anti-apoptotic BCL-2 family proteins in vitro and in cells has been also evaluated previously. Recently, the efficacy and toxicity in mice of gossypol and apogossypol were compared. Preclinical in vivo data show that apogossypol has better efficacy and reduced toxicity compared to gossypol, as well as better single-dose pharmacokinetic characteristics, including, superior blood concentrations over time compared to gossypol, due to slower clearance. These observations indicate that apogossypol is a promising lead compound for cancer therapy.

BCL-2 family members are also believed to be involved in inflammatory disorders. For example, BCL-2 family members have been shown to play roles in neutrophil apoptosis and inflammatory accumulation. In several inflammatory diseases, the delay of neutrophil apoptosis is associated with reduced levels of the pro-apoptotic BCL-2 family member BAX. It has been also shown that eosinophils isolated from children with acute asthma had an increased expression of the anti-apoptotic protein BCL-2, which was inversely correlated with expiratory flow rate. BCL-2 family proteins are also associated with Crohn's disease. BAX expression is attenuated and BCL-$X_L$ expression is increased in T cells isolated from the lamina propria from patients with Crohn's disease. This shows that inflammatory cell survival, by means of pro-survival and anti-apoptotic signaling mechanisms, are involved in the pathogenesis of inflammatory diseases. Lupus is a complex systemic autoimmune disease, characterized by high levels of anti-DNA and anti-glomerular autoantibodies, activated B and T-cells, and glomerulonephritis. Neutrophils from lupus-susceptible mice display reduced rates of apoptosis. The decreased apopotosis is associated with the altered expression of BCL-2 family proteins contributing to the greater accumulation of neutrophils in the lupus-susceptible mice. Signaling studies using several different lupus strains indicate that multiple signaling pathways are upregulated in lymphocytes and non lymphocytes as disease evolves, including the activation of BCL-2 and BCL-$X_L$. These anti-apoptotic molecules are known to prolong the lifespan of all cells, including autoreactive B and T cells.

In view of these drawbacks and deficiencies of existing BCL-2 inhibitors, new antagonists of anti-apoptotic proteins, such as BCL-2 family proteins, are desired. It is desirable that such new antagonists be safer and more effective than the existing compounds.

SUMMARY OF THE DISCLOSURE

The disclosure addresses these needs by providing new antagonists of anti-apoptotic proteins, including the BCL-2 family of proteins. In our continued attempts to identify novel and effective pan-Bcl-2 antagonists, we have recently prepared a series of compound 2 (Apogossypol) derivatives, that resulted in the chiral compound 4 (8r) as the racemate. We report here on synthesis and evaluation of its optically pure individual isomers. It has been surprisingly found that compound 11 (BI-97C1), is the most potent diastereoisomer of compound 4, and inhibits the binding of BH3 peptides to Bcl-$X_L$, Bcl-2, Mcl-1 and Bfl-1 with IC$_{50}$ values of 0.31, 0.32, 0.20 and 0.62 µM, respectively. This compound also potently inhibits cell growth of human prostate cancer, lung cancer and lymphoma cell lines with EC$_{50}$ values of 0.13, 0.56 and 0.049 µM, respectively and shows little cytotoxicity against bax$^{-/-}$ bak$^{-/-}$ cells. Compound 11 also displays in vivo efficacy in transgenic mice models and also demonstrates superior single-agent antitumor efficacy in a prostate cancer mouse xenograft model. Thus, compound 11 represents an unexpected advance in the development of novel apoptosis-based therapies against cancer.

Thus, in one embodiment the disclosure provides a compound of Formula I:

In another aspect the disclosure provides methods for treating a disease or disorder by administering to a subject in need thereof a therapeutically effective amount of the compound of Formula I.

In another aspect the disclosure provides methods for treating a disease or disorder by administering to a subject in need thereof a therapeutically effective amount of the compound of Formula I, wherein the disease or the disorder is cancer.

In another aspect the disclosure provides methods for treating a disease or disorder by administering to a subject in need thereof a therapeutically effective amount of the compound of Formula I, wherein the disease or the disorder is cancer, and wherein the cancer is, but not limited to, lung cancer, breast cancer, prostate cancer, renal cancer, pancreatic cancer, skin cancer, melanomas, leukemia, or lymphomas.

In another aspect the disclosure provides methods for treating a disease or disorder by administering to a subject in need thereof a therapeutically effective amount of the compound of Formula I, wherein the treatment includes inhibition of activity of at least one BCL-2 family protein.

In another aspect the disclosure provides methods for treating a disease or disorder by administering to a subject in need thereof a therapeutically effective amount of the compound of Formula I, further comprising administering the compound of Formula I in combination with an anti-cancer agent.

In another aspect the disclosure provides methods for treating cancer or an autoimmune disease in a subject having at least one elevated BCL-2 family protein expression level, the method comprising the step of administering to the subject a therapeutically effective amount of the compound of Formula I.

In another aspect the disclosure provides methods for treating cancer or an autoimmune disease in a subject having at least one elevated BCL-2 family protein expression level, the method comprising the step of administering to the subject a therapeutically effective amount of the compound of Formula I, further comprising determining whether the subject is responsive to a therapy that utilizes the compound or compo-

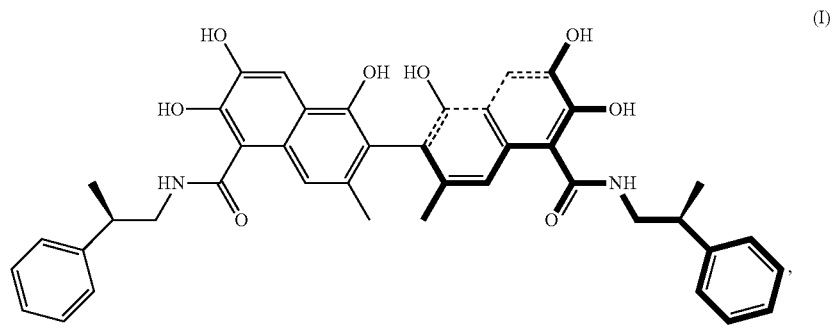

(I)

or a pharmaceutically acceptable salt thereof, specifically where both carbon chiral centers have the R configuration and the atropoisomer along the bi-naphthylene bond is (—).

In another aspect the disclosure provides pharmaceutical compositions including the compound of Formula I and a pharmaceutically acceptable excipient.

sition, comprising determining the level of at least one of the BCL-2 family protein in the subject and comparing to a normal control sample, wherein an elevated level is indicative of a subject responsive to the therapy.

In another aspect the disclosure provides methods for treating cancer or an autoimmune disease in a subject having at least one elevated BCL-2 family protein expression level, the method comprising the step of administering to the subject a therapeutically effective amount of the compound of Formula I, further comprising determining whether the subject is responsive to a therapy that utilizes the compound or composition, comprising determining the level of at least one of the BCL-2 family protein in the subject and comparing to a normal control sample, wherein an elevated level is indicative of a subject responsive to the therapy, and wherein the determination is made based on a sample from the subject.

In another aspect the disclosure provides methods for determining whether a subject is responsive to a therapy that utilizes of the compound of Formula I, the method comprising the step of determining the level of at least one of the BCL-2 family protein in the subject and comparing to a normal control sample, wherein an elevated level is indicative of a subject responsive to the therapy.

In another aspect the disclosure provides methods for determining whether a subject is responsive to a therapy that utilizes of the compound of Formula I, the method comprising the step of determining the level of at least one of the BCL-2 family protein in the subject and comparing to a normal control sample, wherein an elevated level is indicative of a subject responsive to the therapy, and wherein the determination is made based on a sample from the subject.

In another aspect the disclosure provides methods for determining whether a subject is responsive to a therapy that utilizes of the compound of Formula I, the method comprising the step of determining the level of at least one of the BCL-2 family protein in the subject and comparing to a normal control sample, wherein an elevated level is indicative of a subject responsive to the therapy, and wherein the sample is a biological fluid or tumor sample.

In another aspect the disclosure provides methods for determining whether a subject is responsive to a therapy that utilizes of the compound of Formula I, the method comprising the step of determining the level of at least one of the BCL-2 family protein in the subject and comparing to a normal control sample, wherein an elevated level is indicative of a subject responsive to the therapy, and wherein the BCL-2 family polynucleotide or polypeptide is selected from BCL-2, BCL-XL, BCL-W, MCL-1, and BCL-A1.

In another aspect the disclosure provides methods for inducing apoptosis in a cell having a level of at least one of the BCL-2 family protein member greater than levels in a control cell, the method comprising the step of administering to the cell an effective amount of the compound of Formula I, to reduce the level of BCL-2 family protein(s) and induce apoptosis in the cell.

In another aspect the disclosure provides methods for inducing apoptosis in a cell having a level of at least one of the BCL-2 family protein member greater than levels in a control cell, the method comprising the step of administering to the cell an effective amount of the compound of Formula I, to reduce the level of BCL-2 family protein(s) and induce apoptosis in the cell, wherein the cell is a cancer cell.

In another aspect the disclosure provides methods for inducing apoptosis in a cell having a level of at least one of the BCL-2 family protein member greater than levels in a control cell, the method comprising the step of administering to the cell an effective amount of the compound of Formula I, to reduce the level of BCL-2 family protein(s) and induce apoptosis in the cell, wherein the cell is a cancer cell, and wherein the cancer is, but not limited to, lung cancer, breast cancer, prostate cancer, renal cancer, pancreatic cancer, skin cancer, melanomas, leukemia, or lymphomas.

In another aspect the disclosure provides methods for inducing apoptosis in a cell having a level of at least one of the BCL-2 family protein member greater than levels in a control cell, the method comprising the step of administering to the cell an effective amount of the compound of Formula I, to reduce the level of BCL-2 family protein(s) and induce apoptosis in the cell, and wherein the cell is a cell of the immune system.

In another aspect the disclosure provides methods for determining the effectiveness of a therapeutic regimen including administration of the compound of Formula I, the method comprising the step of comparing the level of a BCL-2 family protein in a cell of the subject prior to and during treatment with the compound or composition, wherein a decreased level of BCL-2 family protein is indicative of effectiveness of the therapy that utilizes the compound or composition.

In another aspect the disclosure provides methods for determining the effectiveness of a therapeutic regimen including administration of the compound of Formula I, the method comprising the step of comparing the level of a BCL-2 family protein in a cell of the subject prior to and during treatment with the compound or composition, wherein a decreased level of BCL-2 family protein is indicative of effectiveness of the therapy that utilizes the compound or composition, and wherein the subject has cancer.

In another aspect the disclosure provides methods for determining the effectiveness of a therapeutic regimen including administration of the compound of Formula I, the method comprising the step of comparing the level of a BCL-2 family protein in a cell of the subject prior to and during treatment with the compound or composition, wherein a decreased level of BCL-2 family protein is indicative of effectiveness of the therapy that utilizes the compound or composition, wherein the subject has cancer, and wherein the cancer is, but not limited to, lung cancer, breast cancer, prostate cancer, renal cancer, pancreatic cancer, skin cancer, melanomas, leukemia, or lymphomas.

In another aspect the disclosure provides methods for determining the effectiveness of a therapeutic regimen including administration of the compound of Formula I, the method comprising the step of comparing the level of a BCL-2 family protein in a cell of the subject prior to and during treatment with the compound or composition, wherein a decreased level of BCL-2 family protein is indicative of effectiveness of the therapy that utilizes the compound or composition, and wherein the subject has an autoimmune disorder.

In another aspect the disclosure provides methods for treating inflammation in a subject, the method comprising the step of administering to the subject in need of the treatment an effective amount of the compound of Formula I.

In another aspect the disclosure provides methods for treating inflammation in a subject, the method comprising the step of administering to the subject in need of the treatment an effective amount of the compound of Formula I, wherein the subject is afflicted with a condition wherein the condition is lupus erythmatosus, psoriasis, psoriatic arthritis, lupus nephritis, rheumatoid arthritis, multiple sclerosis, ulcerative colitis, myasthenia gravis, ITP, TTP, Grave's disease, Hashimoto's thyroiditis, Crohn's disease, autoimmune hemolytic anemias, insulin dependent diabetes mellitus, glomerulonephritis, rheumatic fever, osteoarthritis, gouty arthritis, dermatitis, bronchitis, rhinitis, asthma, Sjogrens' syndrome, meningitis, adrenoleukodystrophy, CNS vasculitis, mitochondrial myopathies, Amyotrophic Lateral Sclerosis, Alzheimer's disease, or a tumor.

In another aspect the disclosure provides methods for treating inflammation in a subject, the method comprising the step of administering to the subject in need of the compound of Formula I, wherein the subject is afflicted with a condition wherein the condition is lupus erythmatosus, psoriasis, psoriatic arthritis, lupus nephritis, rheumatoid arthritis, multiple sclerosis, ulcerative colitis, myasthenia gravis, ITP, TTP, Grave's disease, Hashimoto's thyroiditis, Crohn's disease, autoimmune hemolytic anemias, insulin dependent diabetes mellitus, glomerulonephritis, rheumatic fever, osteoarthritis, gouty arthritis, dermatitis, bronchitis, rhinitis, asthma, Sjogrens' syndrome, meningitis, adrenoleukodystrophy, CNS vasculitis, mitochondrial myopathies, Amyotrophic Lateral Sclerosis, Alzheimer's disease, or a tumor, and wherein the mitochondrial myopathy is MELAS syndrome, MERF syndrome, Leber's disease, Wernicke's encephalopathy, Rett syndrome, homocystinuria, hyperprolinemia, nonketotic hyperglycinemia, hydroxybutyric aminoaciduria, sulfite oxidase deficiency, or combined systems disease (B12 deficiency).

In another aspect the disclosure provides methods for treating inflammation in a subject, the method comprising the step of administering to the subject in need of the treatment an effective amount of the compound of Formula I, further comprising administering a selective serotonin reuptake inhibitor (SSRI).

In another aspect the disclosure provides methods for preparing the compound of Formula I:

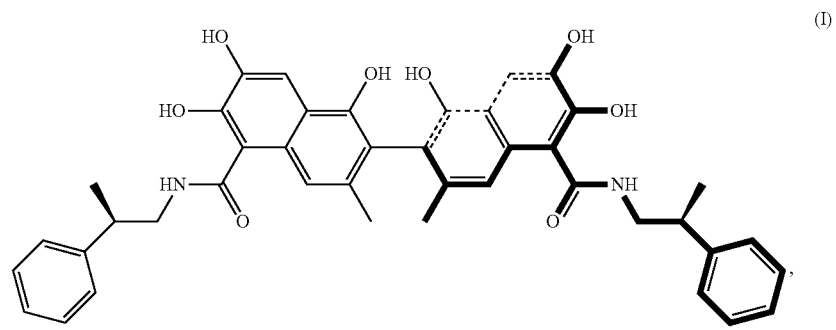

or a pharmaceutically acceptable salt thereof, specifically where both carbon chiral centers have the R configuration and the atropoisomer along the bi-naphthylene bond is (—), the method comprising the steps of:

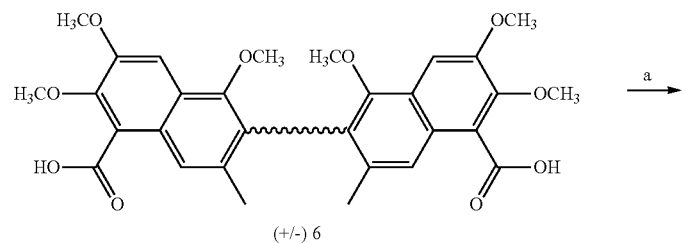

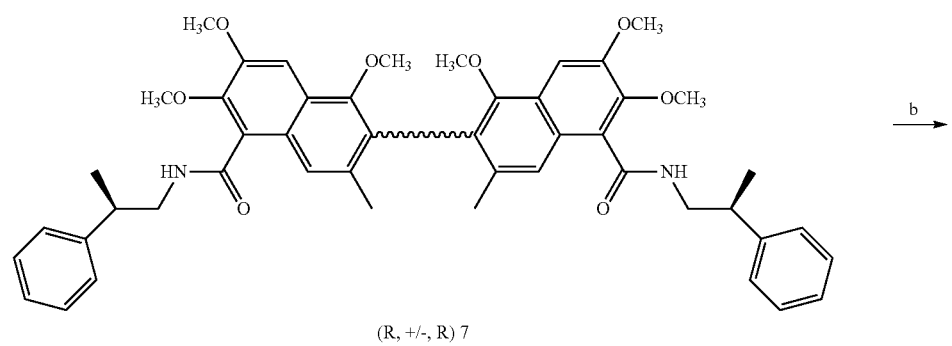

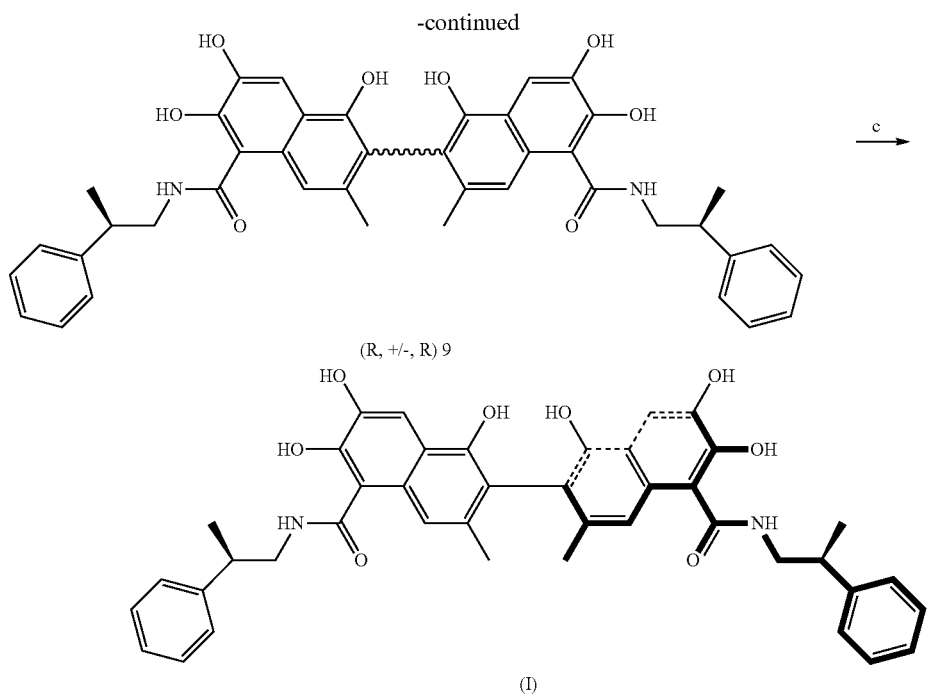

a) coupling the racemic carboxylic acid 6 with optically pure chiral amine (R)-(+)-β-methylphenethylamine in the presence of 1-ethyl-3-(3'-dimethylaminopropyl)carbodiimide (EDCI) to provide atropoisomer compound (R, +/−, R) 7;

b) demethylating atropoisomer compound (R, +/−, R) 7 with boron tribromide to provide atropisomer compound (R, +/−, R) 9; and c) resolving atropisomer compound (R, +/−, R) 9 using liquid chiral column chromatography to provide the compound of Formula I.

In another aspect the disclosure provides methods for isolating the atropisomers of the compound of Formula II:

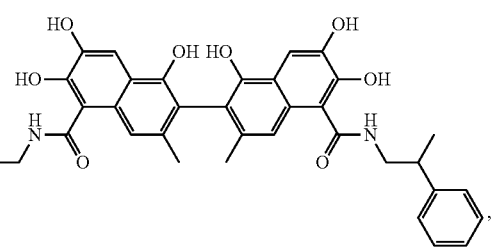

or a pharmaceutically acceptable salt thereof, specifically where both carbon chiral centers have the R configuration and the atropoisomer along the bi-naphthylene bond is (—), the method comprising the steps of:

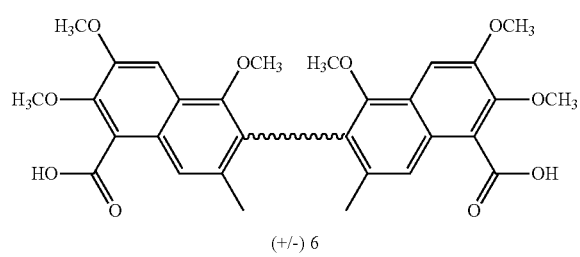

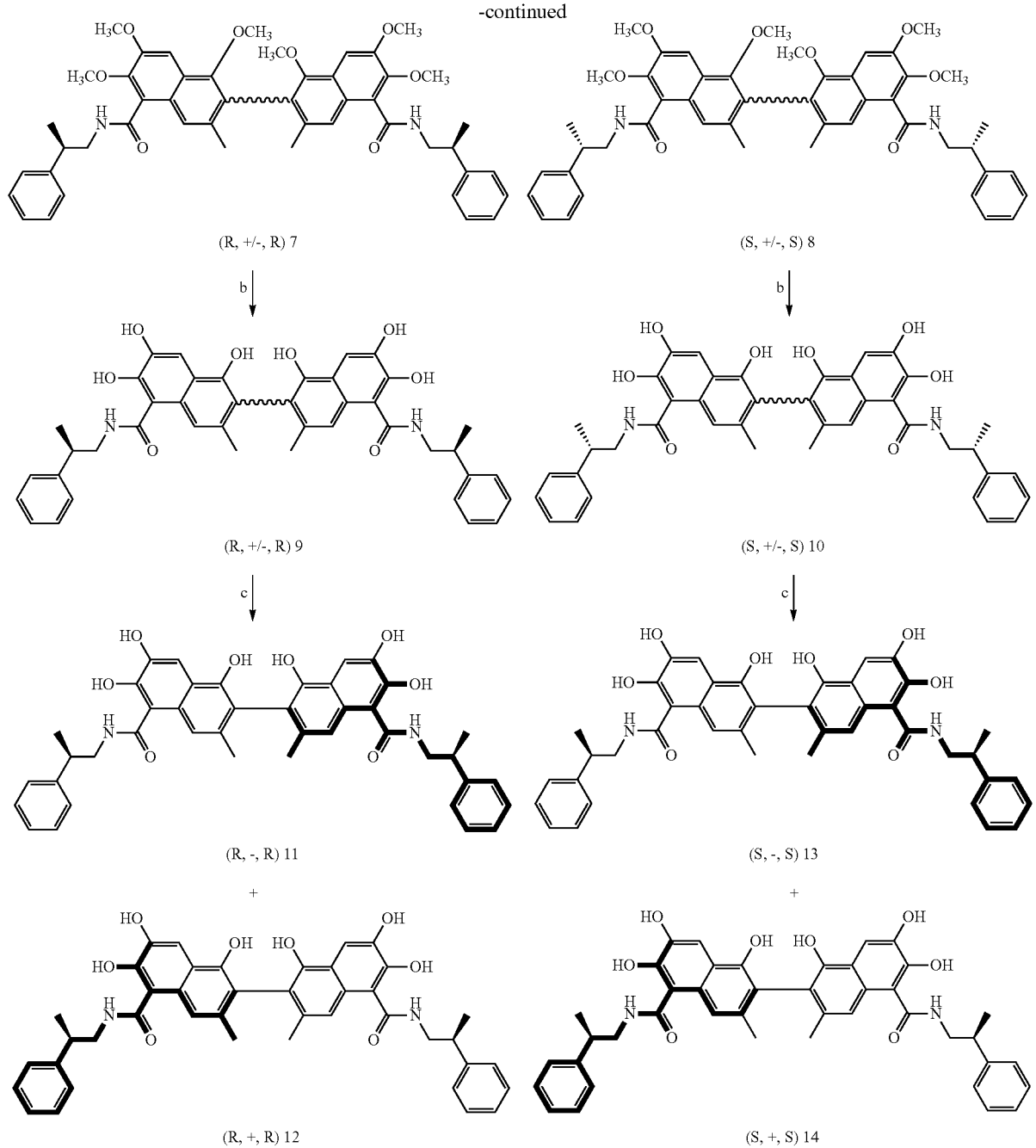

a (R)) coupling the racemic carboxylic acid 6 with optically pure chiral amine (R)-(+)-β-methylphenethylamine in the presence of 1-ethyl-3-(3'-dimethylaminopropyl)carbodiimide (EDCI) to provide atropoisomer compound (R, +/−, R) 7, and a(S)) coupling the racemic carboxylic acid 6 with optically pure chiral amine (S)-(−)-β-methylphenethylamine in the presence of EDCI to provide atropoisomer compound (S, +/−, S) 8;

b) demethylating atropoisomer compound (R, +/−, R) 7 and atropoisomer compound (S, +/−, S) 8 with boron tribromide to provide atropisomer compound (R, +/−, R) 9 and atropisomer compound (S, +/−, S) 10, respectively; and c) resolving atropisomer compound (R, +/−, R) 9 and atropisomer compound (S, +/−, S) 10 using liquid chiral column chromatography to provide the atropisomers of the compound of Formula II, namely (R, −, R) 11, (R, +, R) 12, (S, −, S) 13, and (S, +, S) 14.

DETAILED DESCRIPTION OF THE DISCLOSURE

Figure 1:
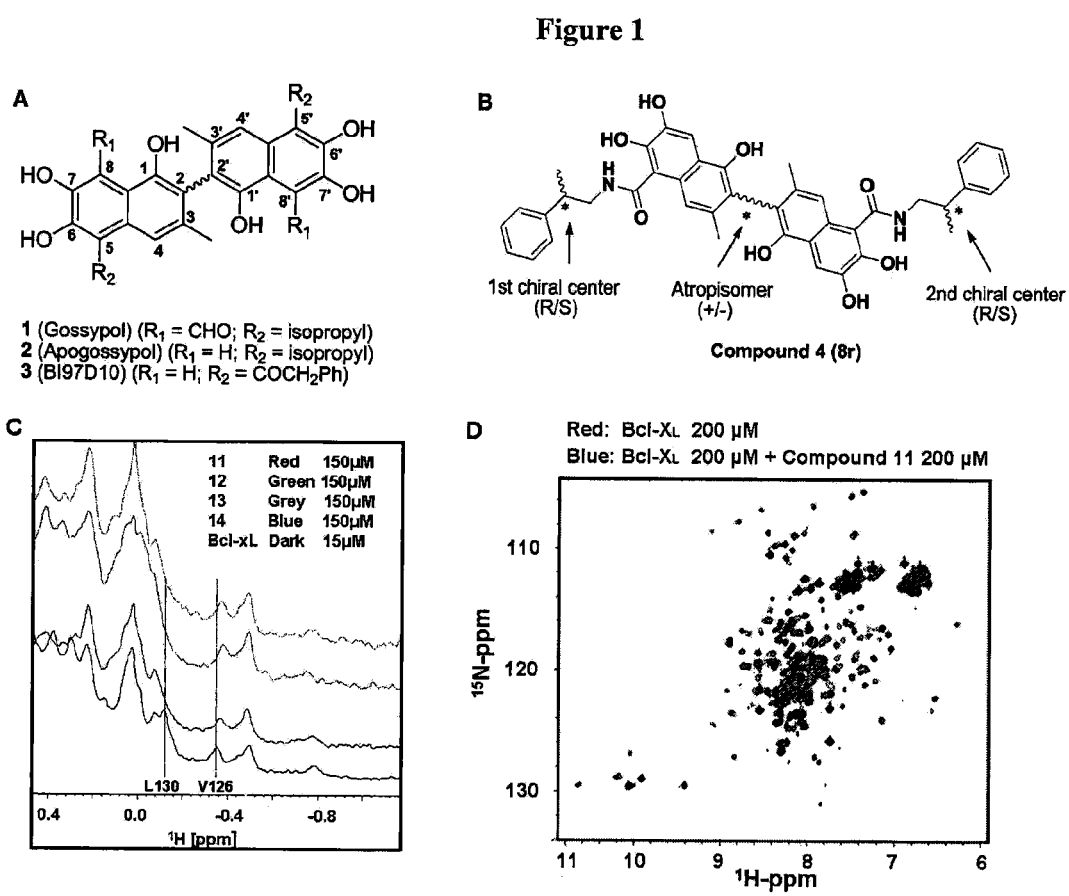
FIG. 1.(A) Structure of compounds 1, 2 and 3. (B) Structure of compound 4 (8r). (C) NMR binding studies. Aliphatic region of the $^1$H-NMR spectrum of Bcl-$X_L$ (15 μM black) and Bcl-$X_L$ in the presence of compound 11 (150 μM, red), 12 (150 μM, green), 13 (150 μM, grey) and 14 (150 μM, blue). (D) Superposition of 2D [$^{15}$N,$^1$H]-TROSY spectra of free Bcl-$X_L$ (200 μM; red) and after addition of compound 11 (200 μM; blue).

Unless otherwise defined, scientific and technical terms used in connection with the disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, definitions and abbreviations further apply:

The term "patient" refers to organisms to be treated by the methods of the disclosure. Such organisms include, but are not limited to, humans and other mammals. In the context of the disclosure, the term "subject" generally refers to an individual who will receive or who has received treatment described herein (e.g., administration of the compounds of the disclosure, and optionally one or more additional therapeutic agents).

The terms "treating" or "treatment" in reference to a particular disease includes prevention of the disease.

The term "BCL-2 family of proteins" refers to the family of proteins that currently includes at least the following six proteins: BCL-$X_L$, BCL-2, BCL-W, BCL-B, BFL-1, and MCL-1.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The compounds of the disclosure may exist as salts. The disclosure includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, mono-hydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methane-sulfonic, and the like. Also included are salts of amino acids such as arginate and the like, and salts of organic acids like glucuronic or galactunoric acids and the like. Certain specific compounds of the disclosure contain both basic and acidic functionalities that allow the compounds to be converted into either base or acid addition salts.

The term "pharmaceutically acceptable salts" is meant to include salts of active compounds which are prepared with relatively nontoxic acids or bases, depending on the particular substituent moieties found on the compounds described herein. When compounds of the disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt.

When compounds of the disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the disclosure contain both basic and acidic functionalities that allow the compounds to be converted into either base or acid addition salts.

In addition to salt forms, the disclosure provides compounds, which are in a prodrug form. Prodrugs of the compounds described herein are those compounds that readily undergo chemical changes under physiological conditions to provide the compounds of the disclosure. Additionally, prodrugs can be converted to the compounds of the disclosure by chemical or biochemical methods in an ex vivo environment. For example, prodrugs can be slowly converted to the compounds of the disclosure when placed in a transdermal patch reservoir with a suitable enzyme or chemical reagent.

The neutral forms of the compounds are regenerated by contacting the salt with a base or acid and isolating the parent compound in the conventional manner. The parent form of the compound differs from the various salt forms in certain physical properties, such as solubility in polar solvents.

Certain compounds of the disclosure can exist in unsolvated forms as well as solvated forms, including hydrated forms. In general, the solvated forms are equivalent to unsolvated forms and are encompassed within the scope of the disclosure. Certain compounds of the disclosure may exist in multiple crystalline or amorphous forms. In general, all physical forms are equivalent for the uses contemplated by the disclosure and are intended to be within the scope of the disclosure.

Certain compounds of the disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the disclosure. The compounds of the disclosure do not include those which are known in art to be too unstable to synthesize and/or isolate. The disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another. It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the compounds are within the scope of the disclosure.

Unless otherwise stated, structures depicted herein are also meant to include compounds which differ in the presence of one or more isotopically enriched atoms. For example, compounds having the structures except for the replacement of a hydrogen by a deuterium or tritium, or the replacement of a carbon by $^{13}C$- or $^{14}C$-enriched carbon are within the scope of this disclosure. The compounds of the disclosure may also contain unnatural proportions of atomic isotopes at one or more of atoms that constitute such compounds. For example, the compounds may be radiolabeled with radioactive isotopes, such as for example tritium (3H), iodine-125 ($^{125}I$) or carbon-14 ($^{14}C$). All isotopic variations of the compounds of the disclosure, whether radioactive or not, are encompassed within the scope of the disclosure.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "prodrug" or "pro-drug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

As used herein, the term "apogossypol" is a broad term which includes, without limitation, L-apogossypol, D-apogossypol, racemic apogossypol, S-apogossypol, R-apogossypol, (−) apogossypol and (+) apogossypol, and includes (−) apogossypol that is substantially free of (+) apogossypol.

Throughout the disclosure, when a particular compound is mentioned by name, for example, apogossypol, it is understood that the scope of the disclosure encompasses pharmaceutically acceptable salts, esters, amides, metabolites, or prodrugs of the named compound.

It will be appreciated by those skilled in the art that compounds of the disclosure having a chiral center may exist in and be isolated in optically active and racemic forms. Some compounds may exhibit polymorphism. It is to be understood that the disclosure encompasses any racemic, optically active, polymorphic, or stereoisomeric form, or mixtures thereof, of a compound of the disclosure, which possesses the useful properties described herein. Also, if the named compound comprises a chiral center, the scope of the disclosure also includes compositions comprising the racemic mixture of the two enantiomers, as well as compositions comprising each enantiomer individually, substantially free of the other enantiomer. Thus, for example, contemplated herein is a composition comprising the S enantiomer substantially free of the R enantiomer, or a composition comprising the R enantiomer substantially free of the S enantiomer. As used herein, atropisomers are stereoisomers resulting from hindered rotation about single bonds where the steric strain barrier to rotation is high enough to allow for the isolation of the conformers.

By "substantially free" it is meant that the composition comprises less than 10%, or less than 8%, or less than 5%, or less than 3%, or less than 1% of the minor enantiomer. If the named compound comprises more than one chiral center, the scope of the disclosure also includes compositions comprising a mixture of the various diastereomers, as well as compositions comprising each diastereomer substantially free of the other diastereomers. Thus, for example, commercially available apogossypol is a racemic mixture comprising two separate enantiomers. The recitation of "apogossypol" throughout this disclosure includes compositions that comprise the racemic mixture of apogossypol, compositions that comprise the (+) enantiomer substantially free of the (−) enantiomer, and compositions that comprise the (−) enantiomer substantially free of the (+) enantiomer.

It is well known in the art how to prepare optically active forms (for example, by resolution of the racemic form by recrystallization techniques, by synthesis from optically active starting materials, by chiral synthesis, or by chromatographic separation using a chiral stationary phase) and how to determine the anti cancer activity using the standard tests described herein, or using other similar tests which are well known in the art.

The term "pharmaceutical composition" refers to a mixture of a compound with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "Inflammation" as used herein is a general term for the local accumulation of fluid, plasma proteins, and white blood cells that is initiated by physical injury, infection, or a local immune response. Many different forms of inflammation are associated with different diseases. "Inflammation-associated" diseases include, for example, lupus, psoriasis, rheumatoid arthritis, and inflammatory bowel disease. Other inflammation-associated diseases are discussed herein.

As used herein, the terms "anti-inflammatory agent" refers to any anti-inflammatory compounds that are used in the treatment of inflammation.

"Treatment," as used herein, pertains to the therapeutic administration of the compounds of the disclosure for the prevention, amelioration, or cure of disease.

The term "pharmaceutical agent or drug" as used herein refers to a chemical compound or composition capable of inducing a desired therapeutic effect when properly administered to a patient.

As used herein, "substantially pure" means an object species is the predominant species (i.e., on a molar basis it is more abundant than any other individual species in the composition), and a substantially purified fraction is a composition wherein the object species comprises at least about 50 percent (on a molar basis) of all macromolecular species. Generally, a substantially pure composition will comprise more than about 80 percent of all macromolecular species in the composition, for example, more than about 85%, 90%, 95%, and 99%. The object species may be also purified to essential homogeneity (contaminant species cannot be detected in the composition by conventional detection methods), wherein the composition consists essentially of a single species.

In one embodiment the disclosure provides a compound of Formula I:

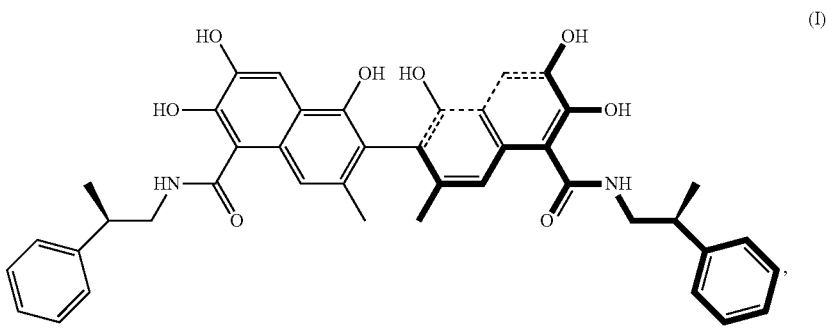

or a pharmaceutically acceptable salt thereof, specifically where both carbon chiral centers have the R configuration and the atropoisomer along the bi-naphthylene bond is (—).

In another aspect the disclosure provides pharmaceutical compositions including the compound of Formula I and a pharmaceutically acceptable excipient.

In another aspect the disclosure provides methods for treating a disease or disorder by administering to a subject in need thereof a therapeutically effective amount of the compound of Formula I.

In another aspect the disclosure provides methods for treating a disease or disorder by administering to a subject in need thereof a therapeutically effective amount of the compound of Formula I, wherein the disease or the disorder is cancer.

In another aspect the disclosure provides methods for treating a disease or disorder by administering to a subject in need thereof a therapeutically effective amount of the compound of Formula I, wherein the disease or the disorder is cancer, and wherein the cancer is, but not limited to, lung cancer, breast cancer, prostate cancer, renal cancer, pancreatic cancer, skin cancer, melanomas, leukemia, or lymphomas.

In another aspect the disclosure provides methods for treating a disease or disorder by administering to a subject in need thereof a therapeutically effective amount of the compound of Formula I, wherein the treatment includes inhibition of activity of at least one BCL-2 family protein.

In another aspect the disclosure provides methods for treating a disease or disorder by administering to a subject in need thereof a therapeutically effective amount of the compound of Formula I, further comprising administering the compound of Formula I in combination with an anti-cancer agent.

In another aspect the disclosure provides methods for treating cancer or an autoimmune disease in a subject having at least one elevated BCL-2 family protein expression level, the method comprising the step of administering to the subject a therapeutically effective amount of the compound of Formula I.

In another aspect the disclosure provides methods for treating cancer or an autoimmune disease in a subject having at least one elevated BCL-2 family protein expression level, the method comprising the step of administering to the subject a therapeutically effective amount of the compound of Formula I, further comprising determining whether the subject is responsive to a therapy that utilizes the compound or composition, comprising determining the level of at least one of the BCL-2 family protein in the subject and comparing to a normal control sample, wherein an elevated level is indicative of a subject responsive to the therapy.

In another aspect the disclosure provides methods for treating cancer or an autoimmune disease in a subject having at least one elevated BCL-2 family protein expression level, the method comprising the step of administering to the subject a therapeutically effective amount of the compound of Formula I, further comprising determining whether the subject is responsive to a therapy that utilizes the compound or composition, comprising determining the level of at least one of the BCL-2 family protein in the subject and comparing to a normal control sample, wherein an elevated level is indicative of a subject responsive to the therapy, and wherein the determination is made based on a sample from the subject.

In another aspect the disclosure provides methods for determining whether a subject is responsive to a therapy that utilizes of the compound of Formula I, the method comprising the step of determining the level of at least one of the BCL-2 family protein in the subject and comparing to a normal control sample, wherein an elevated level is indicative of a subject responsive to the therapy.

In another aspect the disclosure provides methods for determining whether a subject is responsive to a therapy that utilizes of the compound of Formula I, the method comprising the step of determining the level of at least one of the BCL-2 family protein in the subject and comparing to a normal control sample, wherein an elevated level is indicative of a subject responsive to the therapy, and wherein the determination is made based on a sample from the subject.

In another aspect the disclosure provides methods for determining whether a subject is responsive to a therapy that utilizes of the compound of Formula I, the, method comprising the step of determining the level of at least one of the BCL-2 family protein in the subject and comparing to a normal control sample, wherein an elevated level is indicative of a subject responsive to the therapy, and wherein the sample is a biological fluid or tumor sample.

In another aspect the disclosure provides methods for determining whether a subject is responsive to a therapy that utilizes of the compound of Formula I, the method comprising the step of determining the level of at least one of the BCL-2 family protein in the subject and comparing to a normal control sample, wherein an elevated level is indicative of a subject responsive to the therapy, and wherein the BCL-2 family polynucleotide or polypeptide is selected from BCL-2, BCL-XL, BCL-W, MCL-1, and BCL-A1.

In another aspect the disclosure provides methods for inducing apoptosis in a cell having a level of at least one of the BCL-2 family protein member greater than levels in a control cell, the method comprising the step of administering to the cell an effective amount of the compound of Formula I, to reduce the level of BCL-2 family protein(s) and induce apoptosis in the cell.

In another aspect the disclosure provides methods for inducing apoptosis in a cell having a level of at least one of the BCL-2 family protein member greater than levels in a control cell, the method comprising the step of administering to the cell an effective amount of the compound of Formula I, to reduce the level of BCL-2 family protein(s) and induce apoptosis in the cell, wherein the cell is a cancer cell.

In another aspect the disclosure provides methods for inducing apoptosis in a cell having a level of at least one of the BCL-2 family protein member greater than levels in a control cell, the method comprising the step of administering to the cell an effective amount of the compound of Formula I, to reduce the level of BCL-2 family protein(s) and induce apoptosis in the cell, wherein the cell is a cancer cell, and wherein the cancer is, but not limited to, lung cancer, breast cancer, prostate cancer, renal cancer, pancreatic cancer, skin cancer, melanomas, leukemia, or lymphomas.

In another aspect the disclosure provides methods for inducing apoptosis in a cell having a level of at least one of the BCL-2 family protein member greater than levels in a control cell, the method comprising the step of administering to the cell an effective amount of the compound of Formula I, to reduce the level of BCL-2 family protein(s) and induce apoptosis in the cell, and wherein the cell is a cell of the immune system.

In another aspect the disclosure provides methods for determining the effectiveness of a therapeutic regimen including administration of the compound of Formula I, the method comprising the step of comparing the level of a BCL-2 family protein in a cell of the subject prior to and during treatment with the compound or composition, wherein a decreased level of BCL-2 family protein is indicative of effectiveness of the therapy that utilizes the compound or composition.

In another aspect the disclosure provides methods for determining the effectiveness of a therapeutic regimen including administration of the compound of Formula I, the method comprising the step of comparing the level of a BCL-2 family protein in a cell of the subject prior to and during treatment with the compound or composition, wherein a decreased level of BCL-2 family protein is indicative of effectiveness of the therapy that utilizes the compound or composition, and wherein the subject has cancer.

In another aspect the disclosure provides methods for determining the effectiveness of a therapeutic regimen including administration of the compound of Formula I, the method comprising the step of comparing the level of a BCL-2 family protein in a cell of the subject prior to and during treatment with the compound or composition, wherein a decreased level of BCL-2 family protein is indicative of effectiveness of the therapy that utilizes the compound or composition, wherein the subject has cancer, and wherein the cancer is, but not limited to, lung cancer, breast cancer, prostate cancer, renal cancer, pancreatic cancer, skin cancer, melanomas, leukemia, or lymphomas.

In another aspect the disclosure provides methods for determining the effectiveness of a therapeutic regimen including administration of the compound of Formula I, the method comprising the step of comparing the level of a BCL-2 family protein in a cell of the subject prior to and during treatment with the compound or composition, wherein a decreased level of BCL-2 family protein is indicative of effectiveness of the therapy that utilizes the compound or composition, and wherein the subject has an autoimmune disorder.

In another aspect the disclosure provides methods for treating inflammation in a subject, the method comprising the step of administering to the subject in need of the treatment an effective amount of the compound of Formula I.

In another aspect the disclosure provides methods for treating inflammation in a subject, the method comprising the step of administering to the subject in need of the treatment an effective amount of the compound of Formula I, wherein the subject is afflicted with a condition wherein the condition is lupus erythmatosus, psoriasis, psoriatic arthritis, lupus nephritis, rheumatoid arthritis, multiple sclerosis, ulcerative colitis, myasthenia gravis, ITP, TTP, Grave's disease, Hashimoto's thyroiditis, Crohn's disease, autoimmune hemolytic anemias, insulin dependent diabetes mellitus, glomerulonephritis, rheumatic fever, osteoarthritis, gouty arthritis, dermatitis, bronchitis, rhinitis, asthma, Sjogrens' syndrome, meningitis, adrenoleukodystrophy, CNS vasculitis, mitochondrial myopathies, Amyotrophic Lateral Sclerosis, Alzheimer's disease, or a tumor.

In another aspect the disclosure provides methods for treating inflammation in a subject, the method comprising the step of administering to the subject in need of the treatment an effective amount of the compound of Formula I, wherein the subject is afflicted with a condition wherein the condition is lupus erythmatosus, psoriasis, psoriatic arthritis, lupus nephritis, rheumatoid arthritis, multiple sclerosis, ulcerative colitis, myasthenia gravis, ITP, TTP, Grave's disease, Hashimoto's thyroiditis, Crohn's disease, autoimmune hemolytic anemias, insulin dependent diabetes mellitus, glomerulonephritis, rheumatic fever, osteoarthritis, gouty arthritis, dermatitis, bronchitis, rhinitis, asthma, Sjogrens' syndrome, meningitis, adrenoleukodystrophy, CNS vasculitis, mitochondrial myopathies, Amyotrophic Lateral Sclerosis, Alzheimer's disease, or a tumor, and wherein the mitochondrial myopathy is MELAS syndrome, MERF syndrome, Leber's disease, Wernicke's encephalopathy, Rett syndrome, homocystinuria, hyperprolinemia, nonketotic hyperglycinemia, hydroxybutyric aminoaciduria, sulfite oxidase deficiency, or combined systems disease (B12 deficiency).

In another aspect the disclosure provides methods for treating inflammation in a subject, the method comprising the step of administering to the subject in need of the treatment an effective amount of the compound of Formula I, further comprising administering a selective serotonin reuptake inhibitor (SSRI).

In another aspect the disclosure provides methods for preparing the compound of Formula I:

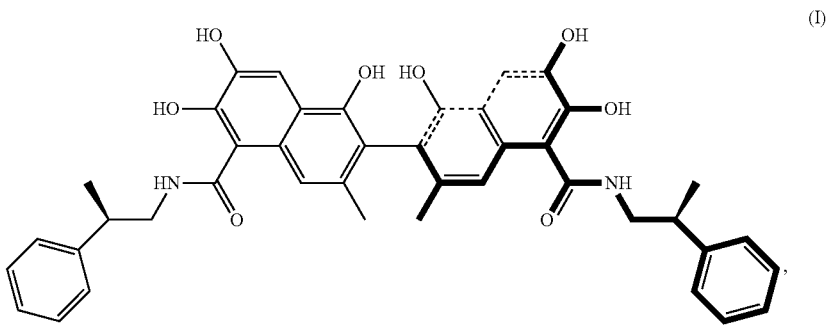

or a pharmaceutically acceptable salt thereof, specifically where both carbon chiral centers have the R configuration and the atropoisomer along the bi-naphthylene bond is (—), the method comprising the steps of:

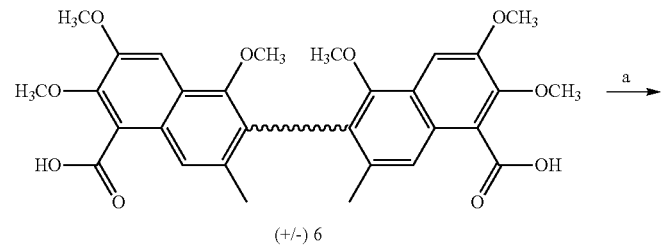

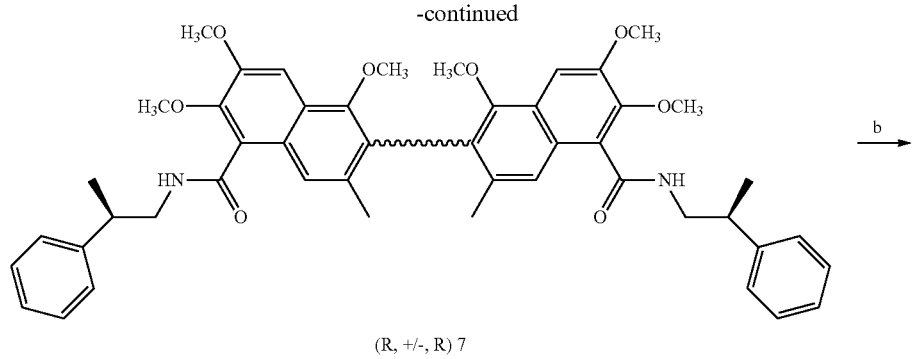

(R, +/−, R) 7

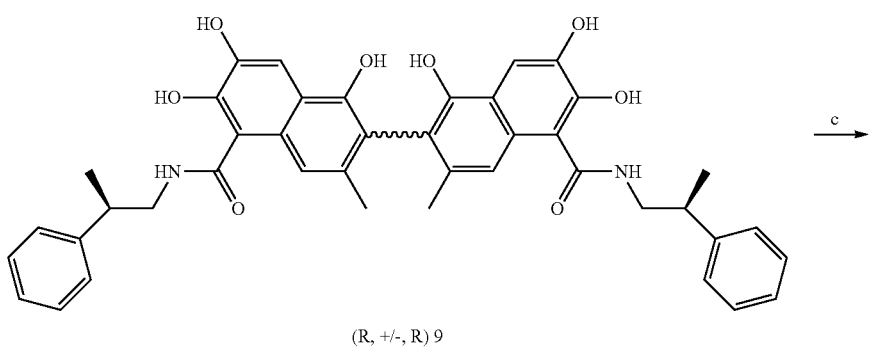

(R, +/−, R) 9

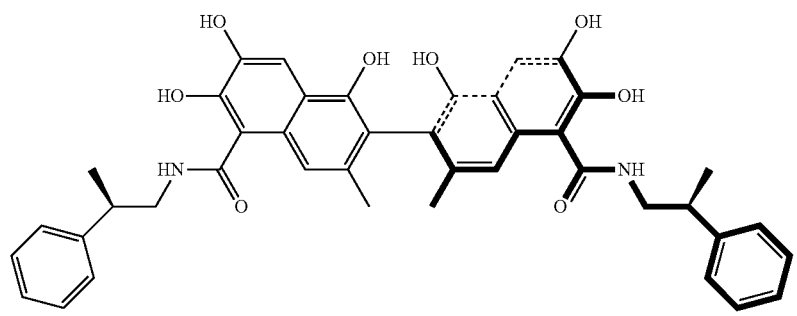

(I)

a) coupling the racemic carboxylic acid 6 with optically pure chiral amine (R)-(+)-β-methylphenethylamine in the presence of 1-ethyl-3-(3'-dimethylaminopropyl)carbodiimide (EDCI) to provide atropoisomer compound (R, +/−, R) 7;

b) demethylating atropoisomer compound (R, +/−, R) 7 with boron tribromide to provide atropisomer compound (R, +/−, R) 9; and c) resolving atropisomer compound (R, +/−, R) 9 using liquid chiral column chromatography to provide the compound of Formula I.

In another aspect the disclosure provides methods for isolating the enantiomers of the compound of Formula II:

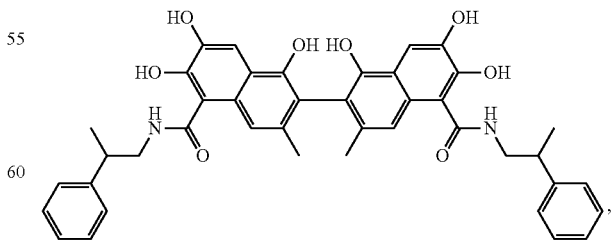

(II)

or a pharmaceutically acceptable salt thereof, the method comprising the steps of:

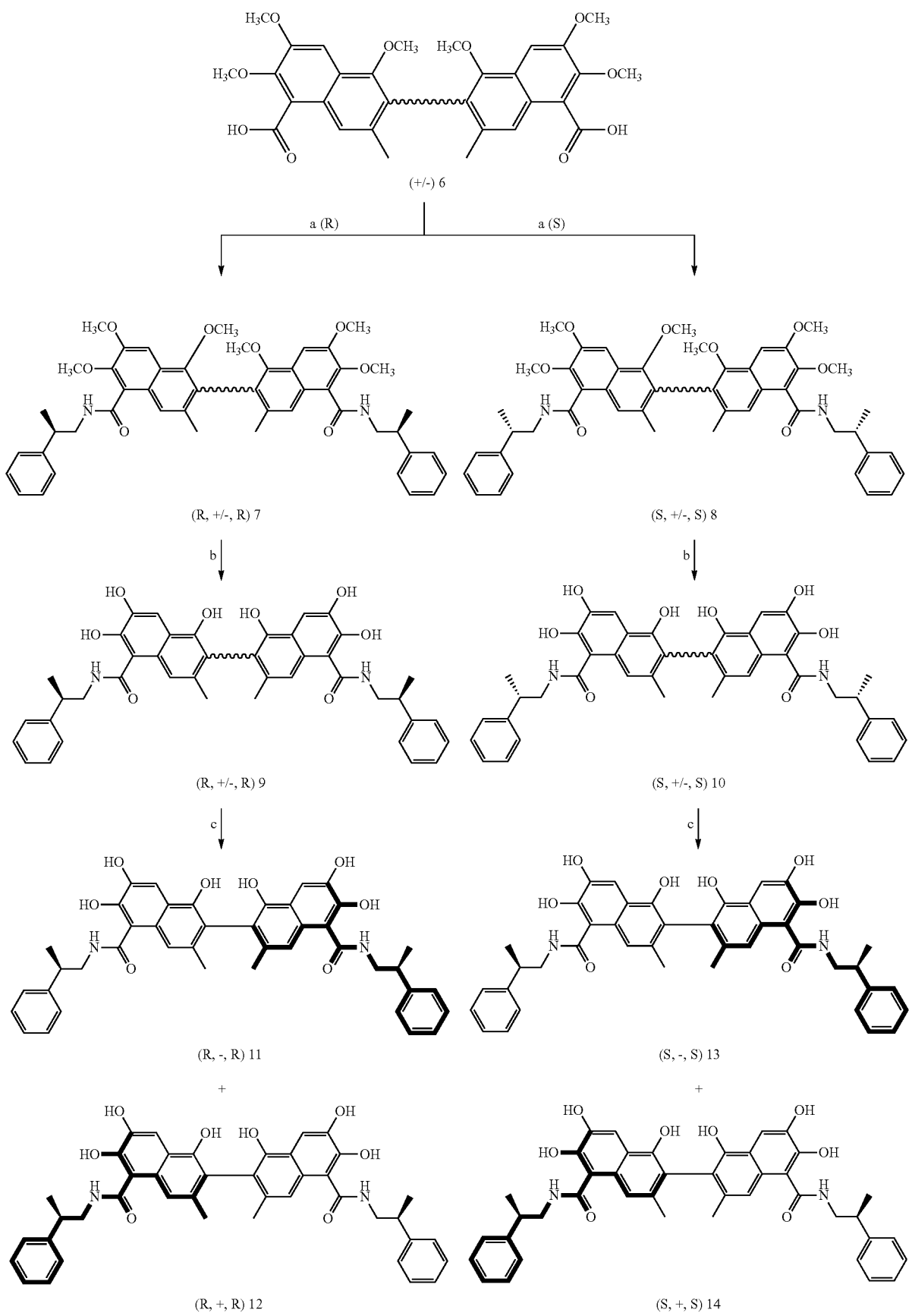

a (R)) coupling the racemic carboxylic acid 6 with optically pure chiral amine (R)-(+)-β-methylphenethylamine in the presence of 1-ethyl-3-(3'-dimethylaminopropyl)carbodiimide (EDCI) to provide atropoisomer compound (R, +/−, R) 7, and a (S)) coupling the racemic carboxylic acid 6 with optically pure chiral amine (S)-(−)-β-methylphenethylamine in the presence of EDCI to provide atropoisomer compound (S, +/−, S) 8;

b) demethylating atropoisomer compound (R, +/−, R) 7 and atropoisomer compound (S, +/−, S) 8 with boron tribromide to provide atropisomer compound (R, +/−, R) 9 and atropisomer compound (S, +/−, S) 10, respectively; and c) resolving atropisomer compound (R, +/−, R) 9 and atropisomer compound (S, +/−, S) 10 using liquid chiral column chromatography to provide the enantiomers of the compound of Formula II, namely (R, −, R) 11, (R, +, R) 12, (S, −, S) 13, and (S, +, S) 14.

Programmed cell-death (apoptosis) plays critical roles in the maintenance of normal tissue homeostasis, ensuring a proper balance of cell production and cell loss.[1,2] Defects in the regulation of programmed cell death promote tumorgenesis, and also contribute significantly to chemoresistance.[3,4] B-cell lymphoma/leukemia-2 (Bcl-2) family proteins are central regulators of this process.[5-7] To date, six anti-apoptotic members of the Bcl-2 family have been identified and characterized, including Bcl-2, Bcl-$X_L$, Mcl-1, Bfl-1, Bcl-W and Bcl-B. Given that over-expression of anti-apoptotic Bcl-2 family proteins occurs in many human cancers and leukemias, these proteins are very attractive targets for the development of novel anticancer agents.[8-10]

Members of the Bcl-2 family proteins also include pro-apoptotic effectors such as Bak, Bax, Bad, Bim and Bid that are antagonized by anti-apoptotic Bcl-2 family proteins via heterodimerization[3] involving a hydrophobic crevice on the surface of anti-apoptotic Bcl-2 family proteins and the alpha-helix BH3 dimerization domain of pro-apoptotic members.[5] Thus, molecules that mimic the BH3 domain of pro-apoptotic proteins may be effective in either inducing apoptosis and/or in abrogating the ability of anti-apoptotic Bcl-2 proteins to inhibit cancer cell death.

The natural product Gossypol (1) shown in FIG. 1A, has been reported to be a potent inhibitor of Bcl-2, Bcl-$X_L$ and Mcl-1, functioning as a BH3 mimic[11-15]. The (−) atropisomer of this compound is currently in phase II clinical trials (AT101), and displays single-agent antitumor activity in patients with advanced malignancies.[13-15] Given that Gossypol (1) may have off-target effects likely due to two reactive aldehyde groups, Apogossypol (2) also shown in FIG. 1A, was desgined as a molecule that lacks these aldehydes, but retains activity against anti-apoptotic Bcl-2 family proteins in vitro.[16] Recently, the efficacy and toxicity of Gossypol (1) and Apogossypol (2) in mice was studied. The preclinical in vivo data shows that Apogossypol (2) has superior efficacy and markedly decreased toxicity compared to Gossypol (1).[17] Also evaluated was the single-dose pharmacokinetic characteristics of Apogossypol (2) in mice. It was found that Apogossypol (2) displayed superior blood concentrations over time compared to Gossypol (1) due to slower clearance.[18]

The separation and characterization of atropisomers of Apogossypol (2) has been examined.[19] These studies revealed that the racemic compound Apogossyol (2) is as effective as its individual isomers in vitro.[19] Also studied were the synthesis and evaluation of 5,5' amide and ketone substituted Apogossypol (2) derivatives.[20,21] Among these derivatives, it was found that compound 3 (BI-79D10) and compound 4 (80[20,21] as shown in FIGS. 1A and 1B, displayed improved in vitro and in vivo efficacy compared to Apogossypol (2). Compound 4 however, has three centers of chirality generated from the 2-phenyl propyl groups, and is a mixture of diastereisomers. In addition, compound 4 displays axial chirality due to restricted rotation around the binaphthyl bond. Therefore, it was attractive to explore whether optically pure isomers of compound 4 presented different in vitro and in vivo activities.

Chirality has a significant effect on the behavior of compounds in vitro and in vivo partially because different enantiomers and diastereoisomers have different unexpected physical, chemical and pharmacology properties. In principle, different enantiomers or diastereoisomers should be treated as different compounds. Indeed, the (−) atropisomer of Gossypol (1) displayed a markedly differential activity compared to its natural racemic mixture. On the basis of these premises, we prepared and isolated the four optically pure isomers (11-14) of compound 4 as provided in Scheme 1, and further investigaged their in vitro and in vivo activities.

Scheme 1

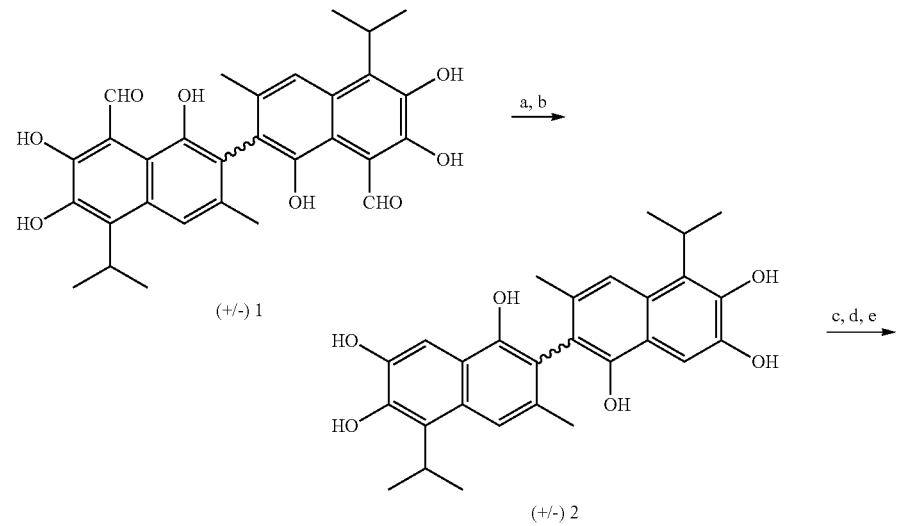

-continued
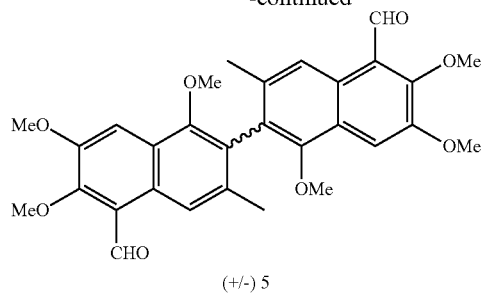
(+/−) 5
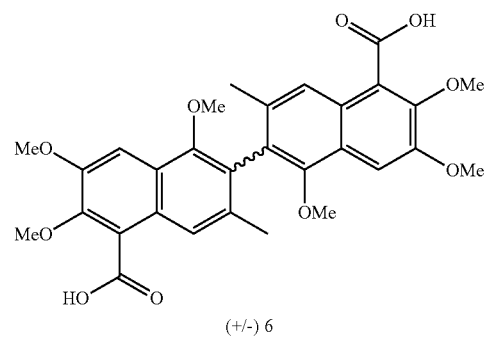
(+/−) 6
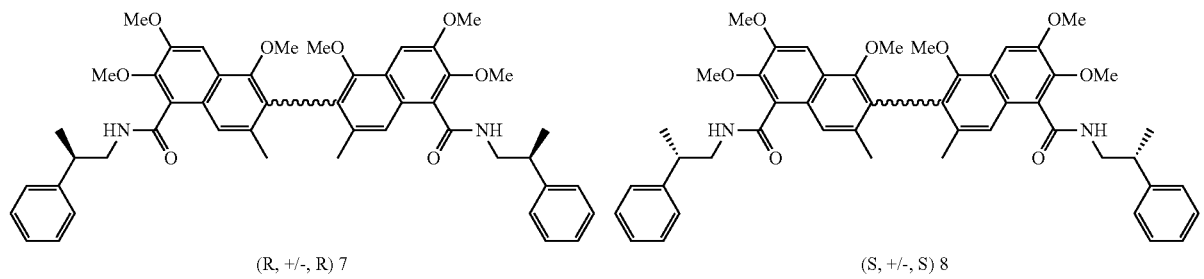
(R, +/−, R) 7          (S, +/−, S) 8
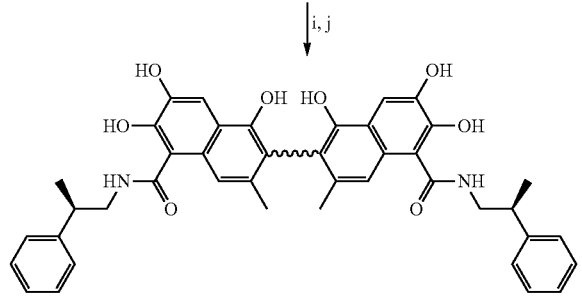
(R, +/−, R) 9          (S, +/−, S) 10

-continued

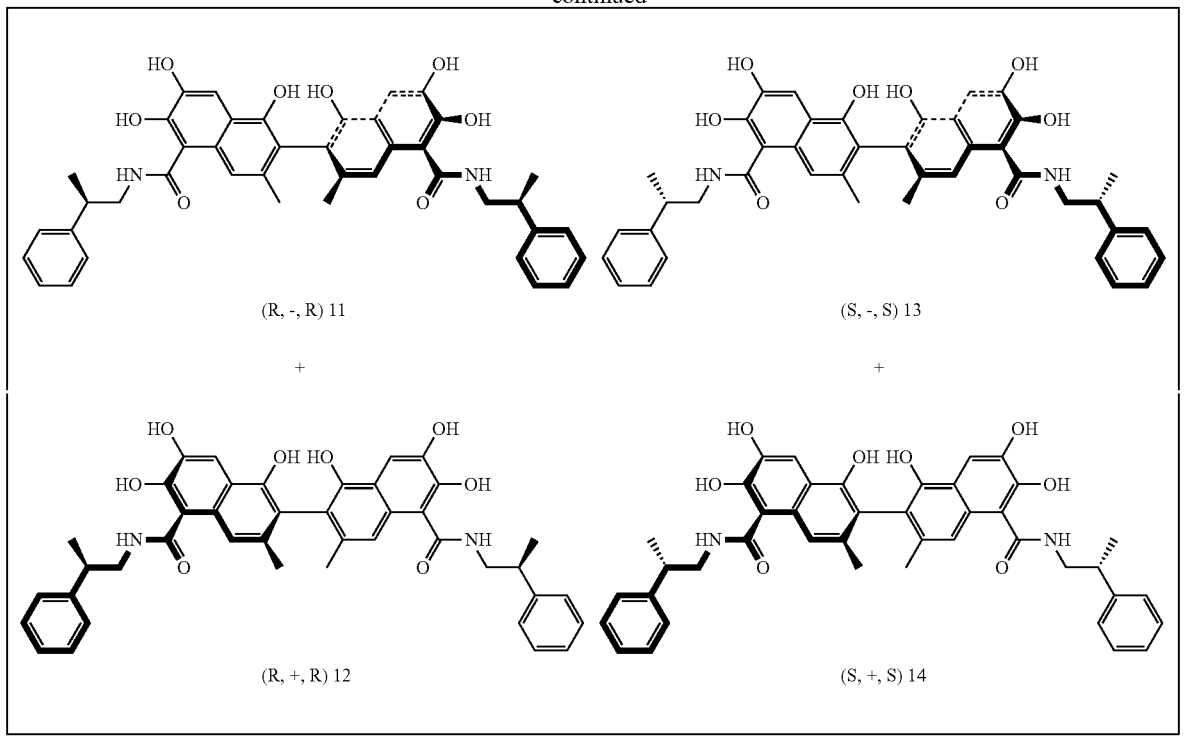

Reagents and conditions: (a) NaOH, $H_2O$, reflux; (b) $H_2SO_4$; (c) DMS, $K_2CO_3$; (d) $TiCl_4$, $Cl_2CHOCH_3$, rt; (e) HCl, $H_2O$ (f) $NaClO_2$, $H_2O_2$, $KH_2PO_4$, $CH_3CN$, rt; (g) (R)-(+)-β-Methylphenethylamine, EDCI, $NH_2R$, HOBT, rt (h) (S)-(−)-β-Methylphenethylamine, EDCI, $NH_2R$, HOBT, rt (i) $BBr_3$, $CH_2Cl_2$ (j) HCl, $H_2O$ (k) Chiral column chromatography separation.

Scheme 1 provides a synthetic route that was developed to prepare the optically pure isomers of compound 4. Synthesis of atropisomers (+/−) 2, (+/−) 5 and (+/−) 6 has been previously reported.[20] As shown in Scheme 1, the racemic carboxylic acid (+/−) 6 was coupled with optically pure chiral amines, (R)-β-methylphenethylamine and (S)-β-methylphenethylamine, respectively, in the presence of 1-ethyl-3-(3'-dimethylaminopropyl)-carbodiimide (EDCI) at room temperature to give atropoisomers (R, +/−, R) 7 and (S, +/−, S) 8, respectively.[22] Subsequent demethylation of the compound (R, +/−, R) 7 and (S, +/−, S) 8 using boron tribromide afforded atropisomers (R, +/−, R) 9 and (S, +/−, S) 10, respectively.[23] The atropisomers (R, +/−, R) 9 were readily resolved using a liquid chiral column chromatography to afford two optically pure isomers (R, −, R) 11 and (R, +, R) 12. The atropisomers (S, +/−, S)-10 were similarly resolved to afford the other two optically pure isomers (S, −, S)-13 and (S, +, S)-14. The optical configuration and purity of each atropisomer was determined using a polorimeter and liquid chiral column chromatography. The optical rotation ([α]) generated by atropisomer (axial chirality) and 2-phenyl propyl groups in compound 4 was approximately +/−18.5° and 33.5°, respectively. Table 1 provides the optical activity and chiral HPLC purity of four diastereoisomers of compound 4.

TABLE 1

| Compd | Optical Activity | Optical rotation [α] (C = 0.1 in EtOH) | HPLC Purity (−):(+) |
|---|---|---|---|
| 14 | (S, +, S) | −9.7 ± 0.5° | 0.49:99.51 |
| 10 | (S, +/−, S) | −29.0 ± 1.0° | 49.43:50.57 |
| 13 | (S, −, S) | −49.0 ± 1.0° | 99.13:0.87 |
| 11 | (R, −, R) | +17.7 ± 0.5° | 99.50:0.5 |
| 9 | (R, +/−, R) | +35.0 ± 0.5° | 49.8:50.2 |
| 12 | (R, +, R) | +53.0 ± 1.5° | 0.39:99.61 |
| 4 | (RS, +/−, RS) | +1.0 ± 0.5° | 48.16:51.84 |
| 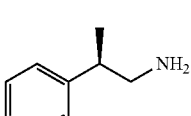 | (R) | +34.2 ± 0.1°[a*] | 99:1 |
| 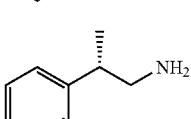 | (S) | −32.8 ± 0.1°[b*] | 99:1 |

[a*]Optical activity [α]22/D + 35.0°, C = 1 in Ethanol, commercially available from Sigma-Aldrich.
[b*]Optical activity [α]22/D − 35.0°, C = 1 in Ethanol, commercially available from Sigma-Aldrich.

As shown in FIG. 1C, the four pure diastereoisomers, namely compounds 11, 12, 13, 14, were first tested by one-dimensional $^1$H nuclear magnetic resonance spectroscopy (1D-$^1$H NMR) binding assays against Bcl-$X_L$, as we reported previously.[24] Compounds 11-14 displayed significant binding to Bcl-$X_L$ in these assays. Compared to other diastereoisomers, compound 11, i.e. the compound of Formula I, induced larger chemical shift perturbations in the active site methyl groups (region between −0.38 and 0.42 ppm) in the one-dimensional $^1$H-NMR spectrum of Bcl-$X_L$. As shown in FIG. 1D, to confirm the result from the one-dimensional $^1$H-NMR binding assay, we also produced uniformly $^{15}$N-labeled Bcl-X$_L$ and measured 2D [$^{15}$N,$^1$H]-TROSY correlation spectra in the absence and presence of compound 11. Compound 11 displayed low to submicromolar binding affinity to Bcl-X$_L$, as qualitatively evaluated by the nature of the shifts at the ligand/protein ratio of 1:1.

Figure 2:
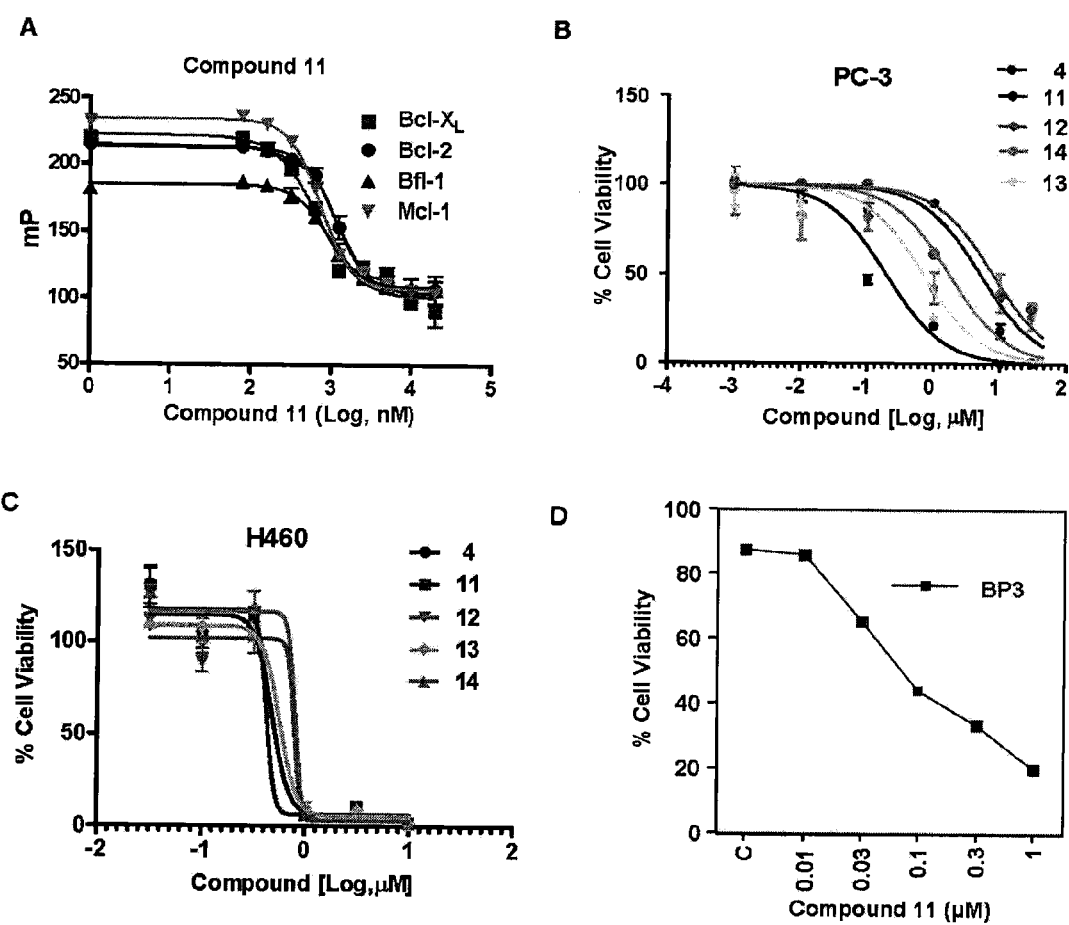
FIG. 2.(A) Fluorescence polarization-based competitive binding curves of compound 11 for Bcl-$X_L$ (red squares), Bcl-2 (blue dots), Bfl-1 (dark up triangle) and Mcl-1 (green up triangle) (B) Inhibition of cell growth by compound 4 (red dots), 11 (blue dots), 12 (green dots), 13 (yellow dots) and 14 (orange dots) in the PC-3 human prostate cancer cell line. Cells were treated for 3 days and cell viability was evaluated using ATP-LITE assay. (C) Inhibition of cell growth by compound 4 (deep blue dots), 11 (red square), 12 (green down triangle), 13 (light blue diamonds) and 14 (grey up triangle) in the H460 human lung cancer cell line. Cells were treated for 3 days and cell viability was evaluated using ATP-LITE assay. (D) Inhibition of cell growth by compound 11 (dark square) in the human BP3 cell line. Apoptosis was monitored by Annexin V-FITC assays.

To further confirm these results, we evaluated the binding affinity of four pure isomers 11-14 using Isothermal Titration Calorimetry assay (ITC), competitive fluorescence polarization assays (FPA) and cell viability assays as shown in FIG. 2, and in Tables 2 and 3. In agreement with NMR binding assays, compound 11 displayed tight binding affinity to Bcl-X$_L$ with a K$_d$ value of 0.11 μM in the ITC assay, which is 4-20 times more potent than other isomers 12-14 in the same assay. Table 2 provides the cross-activity of diastereoisomers of 4 against Bcl-X$_L$, Bcl-2, Mcl-1 and Bfl-1 in Fluorescence Polarization displacement assays and binding to Bcl-xL as measured via Isothermal Titration Calorimetry.

TABLE 2

| Compound | IC$_{50}$ (μM) FPA | | | | K$_d$ (μM) ITC |
|---|---|---|---|---|---|
| IC$_{50}$ | Bcl-X$_L$ | Bcl-2 | Bfl-1 | Mcl-1 | Bcl-X$_L$ |
| 11 | 0.31 ± 0.05 | 0.32 ± 0.05 | 0.62 ± 0.04 | 0.20 ± 0.02 | 0.1 |
| 12 | 0.68 ± 0.09 | 1.14 ± 0.09 | 0.59 ± 0.07 | 0.18 ± 0.02 | 2.4 |
| 13 | 0.44 ± 0.02 | 0.43 ± 0.01 | 0.75 ± 0.07 | 0.24 ± 0.02 | 0.4 |
| 14 | 0.65 ± 0.06 | 0.43 ± 0.03 | 0.77 ± 0.05 | 0.24 ± 0.02 | 2.0 |
| 4 | 0.39 ± 0.02 | 0.66 ± 0.02 | 0.42 ± 0.09 | 0.33 ± 0.02 | ND |

ND = Not determined

Compound 11 also displayed the best inhibitory properties against Bcl-X$_L$ in the FP assay compared to the other pure isomers 12-14 and isomer mixture 4, with an IC$_{50}$ value of 0.31 μM (FIG. 2B). Compound 11 also displayed superior cell membrane permeability compared to other compounds (12-14). Table 4 provides the pasma stability, mcrosomal stability, and cell membrane permeability of diastereoisomers 11-14.

TABLE 4

| Compound | Plasma stability (T = 1 h) | Microsomal Stability (T = 40 min) | Cell Permeability (LogPe) |
|---|---|---|---|
| 11 | 41% | 89.6 ± 7.0% | −6.70 ± 0.30 |
| 12 | 28% | 83.4 ± 8.1% | −7.69 ± 0.14 |
| 13 | 42% | 86.3 ± 7.0% | −7.78 ± 0.06 |
| 14 | 41% | 91.6 ± 1.6% | −7.85 ± 0.13 |

Consistent with NMR binding, ITC, FPA and cell permeability data, compound 11 was more effective compared to other compounds (4 and 12-14) in inhibiting growth of PC3 cells, which expressed high levels of Bcl-X$_L$. The EC$_{50}$ value of compound 11 in killing PC3 cells was 0.13 μM, hence 4-36 fold more potent than other compounds (4 and 12-14). Table 3 provides the efficacy (EC$_{50}$ values in ∝M) of diastereoisomers of compound 4 against prostate cancer cells (PC3), lung cancer cells (H460) and lymphoma cell (BP3).

TABLE 3

| Compound | PC3 $^{a*}$ EC$_{50}$, μM | H460$^{a*}$ EC$_{50}$, μM | BP3$^{b*}$ EC$_{50}$, μM |
|---|---|---|---|
| 11 | 0.13 ± 0.02 | 0.42 ± 0.09 | 0.049 |
| 12 | 4.64 ± 1.07 | 0.78 ± 0.10 | 0.072 |
| 13 | 0.47 ± 0.10 | 0.56 ± 0.08 | 0.31 |
| 14 | 1.61 ± 0.45 | 0.80 ± 0.09 | 0.12 |
| 4 | 2.45 ± 0.50 | 0.47 ± 0.18 | 0.61 |

Figure 3:
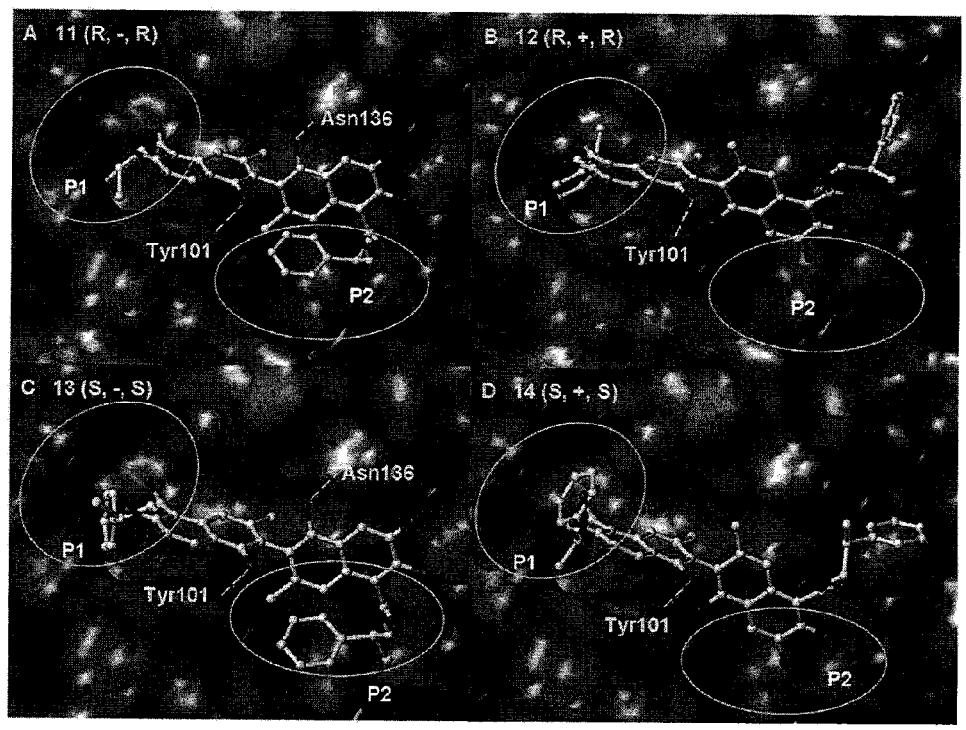
FIG. 3. Molecular docking studies. Stereo views of docked structures of (A) Compound 11. (B) Compound 12. (C) Compound 13. (D) Compound 14 into Bcl-$X_L$ (PDB ID:2YXJ).

$^{a*}$Determined using the ATP-LITE assay
$^{b*}$Determined using Annexin V-FITC and propidium iodide assay As shown in FIG. 3, molecular docking studies of diastereoisomers 11-14 into the BH3 binding groove in Bcl-X$_L$ were performed. These studies suggested that although the left half components of (−) and (+) atropisomers bound similarly to Bcl-X$_L$, their right parts had remarkably different binding models. (−) Atropisomers 11 and 13 not only fully occupied the right hydrophobic pockets (P2) but also formed hydrogen bonding involving their 1' hydroxyl groups on the right naphthalene ring. By contrast, (+) atropisomers 12 and 14 could not occupy the right hydrophobic pocket (P2) or form a hydrogen bond with their 1' hydroxyl groups. The GOLD score of (−) atropisomer 11 was 39.03 which was greater than 34.16 for (+) atropisomer 12. In agreement with FPA and cell data for Bcl-X$_L$, molecular docking studies further suggested that the two centers of chirality generated from 2-phenyl propyl groups had little effect for isomers 11-14 to bind to Bcl-X$_L$. For example, compound 11 and 13 with reverse configurations on 2-phenyl propyl groups had very similar orientations in Bcl-X$_L$ (FIGS. 3A and 3C) and their GOLD score were very similar, with values of 39.03 and 39.78, respectively. This binding trend was also observed for compound 12 and 14 (FIGS. 3B and 3D), with similar gold score of 34.16 and 34.49, respectively. This was not unexpected given that these isomers only differ for the arrangement of a small hydrogen atom and methyl group on the chiral carbon on 2-phenyl propyl group. Based on these observations we focused our effects in the characterization of the (R, −, R) isomer, compound 11, as reported below.

In additional to Bcl-X$_L$, other members of the Bcl-2 family were known to play critical roles in cancer cell survival.[25, 26] Therefore, we further evaluated the binding properties and specificity of isomers 11-14 against Bcl-2, Mcl-1 and Bfl-1 using FP assays (Table 2 and FIG. 2C). All four isomers (11-14) displayed significant displacement properties against Bcl-2, Mcl-1 and Bfl-1 in FP assays with average IC$_{50}$ values of 0.32, 0.22 and 0.65 μM, respectively (Table 2). To confirm the result from FP assays, we also produced uniformly $^{15}$N-labeled Mcl-1 protein and measured 2D [$^{15}$N,$^1$H]-TROSY correlation spectra in the absence and presence of compound 11 (FIG. 2A). Compound 11 displayed a significant binding to Mcl-1, as qualitatively evaluated by the nature of the shifts at the ligand/protein ratio of 2:1. Compound 11 showed inhibitory properties against Bcl-2 compared to other compounds (4 and 12-14), with an IC$_{50}$ value of 0.32 μM in FP assays. Consistent with FPA data, compound 11 displayed best efficacies compared to other compounds (4, 12-14) in inhibiting growth of H460 cells, which expressed high level of Bcl-2.[27-29] The IC$_{50}$ values of 11 in killing H460 cells was 0.42 μM, hence approximately 2-fold more potent than compounds 12 and 14 (Table 2, 3 and FIG. 2C). These observations were consistent with atropisomers (−) 1 and (+) 1, which bound to Bcl-2 with an IC$_{50}$ value of 0.26 and 0.30 μM, respectively, in FPA assays and their EC$_{50}$ value in killing MDA-MB-231 breast cancer cells was around 2.0 and 10.0 μM, respectively.[13] Compound 11 had similar binding affinity as other isomers (12-14) for Mcl-1 and Bfl-1 in FP assays, which could be due to structural difference of their BH3 binding pockets (FIGS. 2B and 2C)[30, 31].

We further evaluated the ability of compounds 11-14 to induce apoptosis of the human BP3 cell line, which originated from a human diffuse large B-cell lymphoma (DLBCL).[20, 26] For these assays, we used Annexin V-FITC and propidium iodide (PI) double staining, followed by flow-cytometry analysis (Table 3). Compounds 11-14 effectively induced apoptosis of the BP3 cell line in a dose-dependent manner (FIG. 2D, Table 3 and FIGS. 3A and 3B). In particular, compound 11 was most effective with an $IC_{50}$ value of 0.049 µM, which was approximately two- to six-fold more potent than other diastereoisomers 12-14 (FIG. 2D, Table 3 and FIGS. 3A and 3B). The mRNA ratio of Bfl-1, Bcl-$X_L$ and Mcl-1 was approximately 10:3:1 in BP3 cell lines.[26] However, we determined by Western Blot that BP3 cells expressed high levels of both Bfl-1 and Mcl-1.[20] In agreement with these observations, the potent dual Bcl-$X_L$ and Bcl-2 antagonist ABT-737[32] displayed no cytotoxic activity against BP3 cell lines presumably because ABT737 was not effective against Mcl-1 and Bfl-1.[25, 32, 33]

Figure 4:
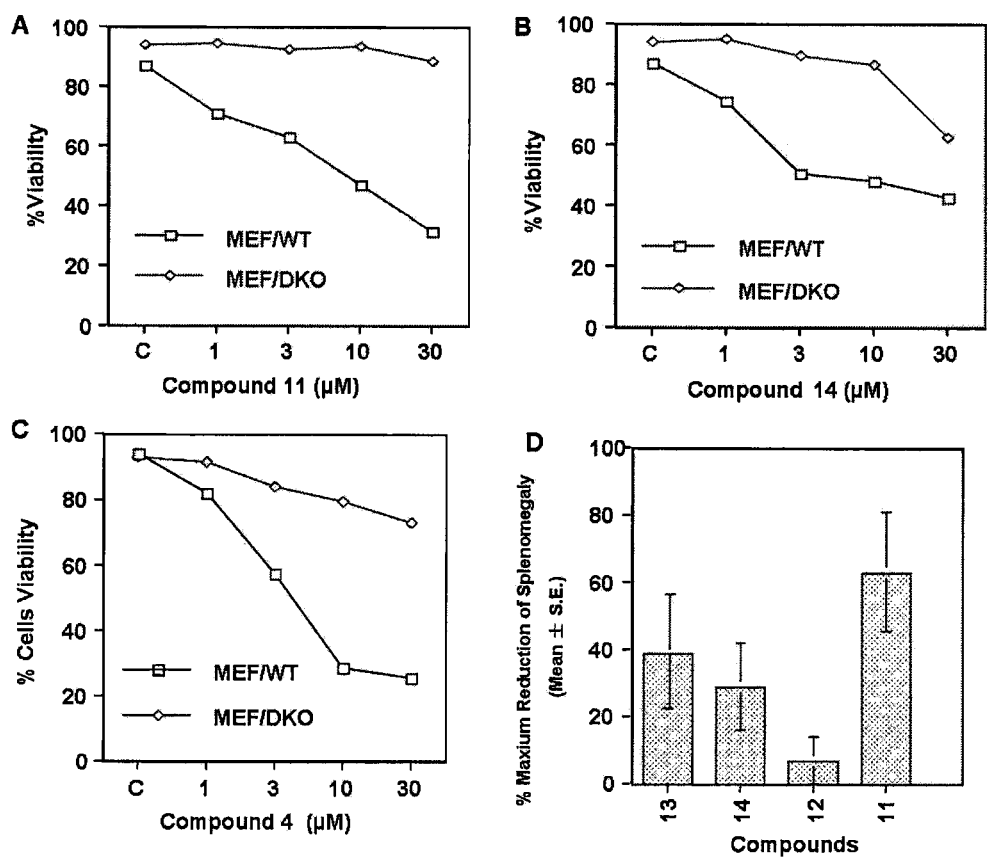
FIG. 4. Mouse embryonic fibroblast cells with wild-type (MEF/WT; dark square) or $bax^{-/-}bak^{-/-}$ double knockout (MEF/DKO, red square) genotypes were treated with compounds 11, 14 and 4 at various concentrations and apoptosis was monitored by Annexin V-FITC assays. (A-C) Compounds 11, 14 and 4. (D) Effects of compounds 11-14 on shrinkage of Bcl-2 mouse spleen at a single intraperitoneal injection dose of 42 mg/kg. All shrinkage data are percentage of maximum reduction of mice spleen size.

We next explored whether pure diastereoisomers 11-14 and diastereoisomer mixture 4 had cytotoxic properties against wild type mouse embryonic fibroblast cells (MEF/WT) and transformed Bax/Bak double knockout MEF cells (MEF/DKO) in which anti-apoptotic Bcl-2 family proteins lacked a cytoprotective phenotype.[34, 35] Compound 11 displayed slight toxicity in Bak/Bak double knockout mouse embryonic fibroblast cells (MEF/DKO) at 30 µM while it killed almost 70% wild type mouse embryonic fibroblast cells (MEF/WT) at same concentration using FITC-Annexin V/PI assays (FIG. 4A), implying that compound 11 only displayed slight off-target effects. By contrast, compound 14 seemed almost equally effective in killing both MEF/WT and MEF/DKO at 30 µM (FIG. 4B), suggesting that other possible killing mechanisms not related to Bcl-2 inhibition were induced by this compound. Accordingly, the mixture of isomers 4 displayed higher cytotoxicity in MEF/DKO cells at 3-30 µM compared to the optically pure isomer 11, indicating that the optically pure isomer was more selective (FIG. 4C).

Figure 5:
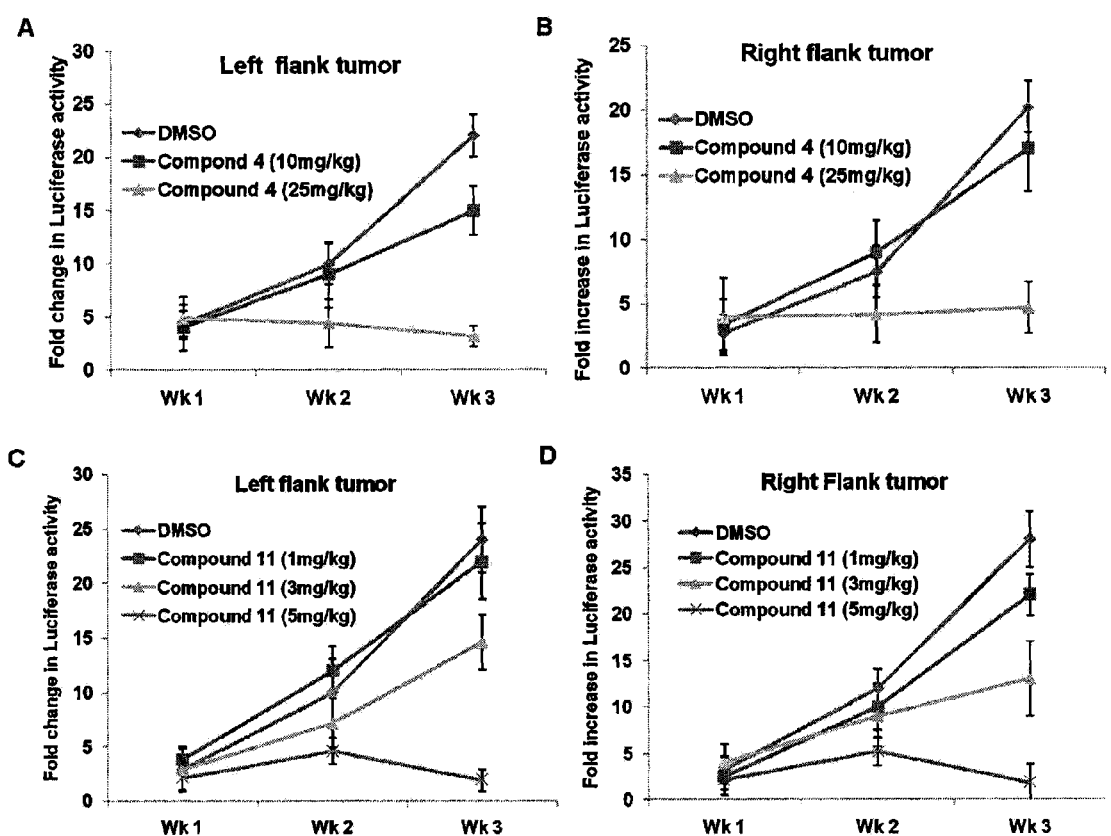
FIG. 5. Characterization of compounds 4 and 11 in tumor xenografts model. Tumor xenografts from M2182 cells were established in athymic nude mice on the left and right flanks. After establishing visible tumors of ~75-mm$^3$, DMSO or compounds (4 or 11) were given (i.p.) every two days (total of nine injections). A minimum of five animals was used per experimental group. For in vivo imaging of tumors the mice were anesthetized and injected i.p. with 150 mg/kg luciferin and light emitted from each tumor was determined in a xenogen system with CCD camera using an integration time of 1 min. Luminescence measurements were made using Living Image software (version 2.50.1; Xenogen). At the end of the experiment, the animals were sacrificed, and the tumors were removed and photographed. (A) Left flank tumor treated with compound 4 at dose of 10 mg/kg and 25 mg/kg, respectively. (B) Right flank tumor treated with compound 4 at dose of 10 mg/kg and 25 mg/kg, respectively. (C) Left flank tumor treated with compound 11 at dose of 1, 3 and 5 mg/kg, respectively. (D) Right flank tumor treated with compound 11 at doses of 1, 3 and 5 mg/kg, respectively.

Next, we examined the pharmacological properties of the isomers as chirality could greatly affect such properties due to stereoselective metabolism. To test the pharmacological properties of diastereoisomers 11-14, we determined their in vitro rat plasma stability, rat microsomal stability, and cell membrane permeability (Table 4). From these studies, we conclude that compound 11 displayed superior cell membrane permeability compared to other diastereoisomers 12-14. The LogPe value of compound 11 was −6.7, which indicates good cell membrane permeability, while LogPe values of other compounds (12-14) were around −7.8, which corresponded to relative poor cell membrane permeability. Compound 11 also displayed relatively good microsomal stability (Table 4) in which the compound degraded 10.4% after 40 minutes incubation in rat microsomal preparations. By contrast, compound 12 displayed decreased plasma and microsomal stability compared to other diastereoisomers. Compound 11 also displayed better chemical stability compared to other compounds (12-14) at different temperatures (FIG. 5).

Using a combination of NMR-based binding assays, FP assays, ITC assays, cytotoxicity assays and preliminary in vitro ADME data, we selected pan-Bcl-2 antagonists to be further tested in vivo models. Unlike currently available antagonists,[32, 36] our compounds were effective in inhibiting several of the anti-apoptotic Bcl-2 proteins, hence were expected to display in vivo efficacy against a variety of mice models of cancer that relied on different Bcl-2 proteins for growth and progression. To test this hypothesis we selected two different models: Bcl-2 transgenic mouse model and prostate cancer xenograft model that relied on Mcl-1 overexpression. B-cells of the B6 transgenic mice overexpressed human Bcl-2 and accumulated in the spleen of mice.[17, 20] Because we had determined that the spleen weight was highly consistent in age- and sex-matched Bcl-2-transgenic mice, varying by only ±2% among control Bcl-2 mice,[17] the spleen weight was used as an end-point for assessing in vivo activity. We tested the in vivo activities of isomers 11-14 in two Bcl-2 transgenic mice with a single intraperitoneal (i.p.) injection at 42 mg/kg. In agreement with in vitro data, compound 11 displayed superior in vivo activity compared to other isomers (12-14) in this model. It induced more than 30% spleen weight reduction compared to ≦20% induced by other diastereoisomers. Since the maximum spleen shrinkage would be no more than 50% in this experimental model,[20] these compounds induced near 65% maximal biological activity, while other isomers 12-14 induced ≦40% of maximum reduction in spleen weight at the same dose. In particular, compound 12 displayed weak in vivo activity, which was in consistent with its relatively weak cell activity and poor pharmacological properties. All mice tolerated the treatment well, with only mild signs of GI toxicity.

As mentioned, current available experimental treatments targeting Bcl-2 proteins failed to address Mcl-1 as a critical regulator of cancer survival. In fact, the potent Bcl-$X_L$/Bcl-2 antagonist ABT-737 (Abbott Laboratories) and the Bcl-2 antisense Genasense (Genta) were not effective against cancer cells that overexpress Mcl-1.[32,36] Therefore, to further examine the therapeutic potential of compound 11 as a single agent against tumors that relied on Mcl-1 for survival, compound 11 was evaluated side by side with compound 4 in a prostate cancer xenograft using the M2182 cell line. M2182 was a tumorigenic variant of normal prostate epithelial P69 cell and highly overexpressed Mcl-1.[37-40] A quantity of 1×10⁶ M2182 cells were injected subcutaneously in the left and right flanks of male athymic nude mice, and the tumors were allowed to grow to an average size of ≈75 mm³ prior to initiation of therapy. Compounds 4 and 11 were administrated (i.p.) every 2 days (total of nine injections) and compound 4 was injected at two doses, 10 and 25 mg/kg while compound 11 was administrated at three lower doses, 1, 3 and 5 mg/kg due to its superior in vitro properties compared to compound 4. Compound 11 and 4 displayed a marked inhibitory effect of tumor size compared with the control group (FIG. 5A-D and FIGS. 5A and 5B). In fact, compound 11 at the dose of 5 mg/kg (FIG. 5A-5D) and compound 4 at the dose of 25 mg/kg (FIGS. 5A and 5B) induced near complete inhibition of tumor growth in both flanks compared with their control groups. As anticipated, compound 11 displayed better tumor growth inhibitory effect compared to compound 4. Even at the dose of 3 mg/kg, compound 11 inhibited tumor growth to ~60% of the tumor volume in the control group (FIG. 5A-5D) while compound 4 displayed weak inhibitory effect of tumor size at the dose of 10 mg/kg (FIGS. 5A and 5B). All mice tolerated the treatment well with no apparent signs of toxicity.

In summary, we synthesized and evaluated four diastereoisomers (11-14) of compound 4 in a variety of in vitro and in vivo assays. The optically pure compound 11 inhibits the binding of BH3 peptides to Bcl-$X_L$, Bcl-2, Mcl-1 and Bfl-1 with $IC_{50}$ values of 0.31, 0.32, 0.20 and 0.62 µM, respectively. The compound 11 also potently inhibits cell growth of human prostate cancer, lung cancer and BP3 B-cell lymphoma cell lines with $EC_{50}$ values of 0.13, 0.56 and 0.049 µM, respectively. The compound 11 displays approximately 20-fold and 12-fold greater efficacy in inhibiting growth of PC-3 and BP3 cell, respectively, compared to the compound 4 which was previously disclosed.[20] Compound 11 also shows less cytotoxicity against bax$^{-/-}$bak$^{-/-}$ cells compared to compound 4, indicating that it kills cancers cells predominantly via the intended mechanism. Compound 11 displays in vivo efficacy in transgenic mice in which Bcl-2 is overexpressed in splenic B-cells and also demonstrats superior single-agent antitumor efficacy compared to compound 4 in a prostate cancer mouse xenograft model that depends on Mcl-1 for survival. Considering the critical roles of anti-apoptotic Bcl-2 family proteins in tumorgenesis, chemoresistance, and the potent inhibitory activity of compound 11 against anti-apoptotic Bcl-2 family proteins, compound 11 is useful in the development of novel apoptosis-based cancer therapies.

In other aspects the disclosure provides pharmaceutical compositions. The pharmaceutical compositions may comprise any of the disclosed compounds, or pharmaceutically acceptable salts, hydrates, or solvates thereof, and a pharmaceutically acceptable diluent or carrier. The pharmaceutical compositions can be used to treat cancer. The pharmaceutical compositions can further optionally include one or more additional therapeutic anti-cancer agents, including, but not limited to, such agents as (1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); (2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); (3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; (4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); (5) enzymes, including, L-asparaginase, and hydroxyurea, etc.; (6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); (7) platinum compounds (e.g., Cisplatin and Carboplatin, etc.); (8) monoclonal antibodies conjugated with anticancer drugs, toxins, and/or radionuclides, etc.; (9) biological response modifiers (e.g., interferons [e.g., IFN-.alpha., etc.] and interleukins [e.g., IL-2, etc.], etc.); (10) adoptive immunotherapy; (11) hematopoietic growth factors; (12) agents that induce tumor cell differentiation (e.g., all-trans-retinoic acid, etc.); (13) gene therapy agents; 14) antisense therapy agents; (15) tumor vaccines; (16) agents directed against tumor metastases (e.g., Batimistat, etc.); (17) inhibitors of angiogenesis, and (18) selective serotonin reuptake inhibitors (SSRI's).

Non-limiting examples of suitable SSRIs that may be used include sertraline (e.g., sertraline hydrochloride, marketed under the trademark "Zoloft®" by Pfizer, Inc.) or sertraline metabolite, fluvoxamine (e.g., fluvoxamine melate, marketed under the trademark "Luvox®" by Solvay Pharmaceuticals, Inc.), paroxetine (e.g., paroxetine hydrochloride, marketed under the trademark "Paxil®" by SmithKline Beecham Pharmaceuticals, Inc.), fluoxetine (e.g., fluoxetine hydrochloride, marketed under the trademarks "Prozac®" or "Sarafem®" by Eli Lilly and Company) and citalopram (e.g., citalopram hydrobromide, marketed under the trademark "Celexa®" by Forest Laboratories, Parke-Davis, Inc.), and metabolites thereof. Additional examples include venlafaxine (e.g., venlafaxine hydrochloride marketed under the trademark "Effexor®" by Wyeth-Ayerst Laboratories), mirtazapine (e.g., marketed under the trademark "Remeron®" by Organon, Inc.), buspirone (e.g., buspirone hydrochloride marketed under the trademark "Buspar®" by Bristol-Myers Squibb), trazodone (e.g., trazodone hydrochloride marketed under the trademark "Desyrel®" by Bristol-Myers Squibb and Apothecon), nefazadone (e.g., nefazodone hydrochloride marketed under the trademark "Serzon®" by Bristol-Myers Squibb), clomipramine (e.g., clomipramine hydrochloride marketed under the trademark "Anafranil®" by Novopharm, LTD, Ciba, and Taro Pharmaceuticals), imipramine (e.g., imipramine hydrochloride marketed under the trademark "Tofranil®" by Glaxo-Welcome, Inc.), nortriptyline (e.g., Nortriptyline hydrochloride marketed under the trademark "Nortrinel®" by Lundbeck), mianserine (e.g., marketed under the trademark "Tolvon®" by Organon, Inc.), duloxetine (e.g., duloxetine hydrochloride marketed by Eli Lilly and Company), dapoxetine (e.g., dapoxetine hydrochloride marketed by ALZA Corporation), litoxetine (e.g., litoxetine hydrochloride marketed by Synthelabo Recherche (L.E.R.S.), Bagneux, France.), femoxetine, lofepramine (e.g., marketed under the trademark "Gamonil®" by MERCK & Co., Inc.), tomoxetine (e.g., marketed by Eli Lilly and Company). The disclosure encompasses SSRIs that are currently used, or those later discovered or formulated. SSRIs, including those listed herein, may be administered orally in an amount between about 2 mg and about 2,500 mg daily.

In the broad sense, any cancer or tumor (e.g. hematologic and solid tumors) may be treated according to the embodiments of the disclosure. Exemplary cancers that may be treated according to embodiments of the disclosure include, but are not limited to, head and neck cancer, brain cancer (e.g. glioblastoma multifoma) breast cancer, colorectal cancer, esophageal cancer, gastric cancer, hepatic cancer, bladder cancer, cervical cancer, endometrial cancer, lung cancer (non-small cell), ovarian cancer and other gynological cancers (e.g. tumors of the uterus and cervix), pancreatic cancer, prostate cancer, renal cancer, choriocarcinoma (lung cancer), skin cancer (e.g. melanoma, basal cell carcinoma), hairy cell leukemia, chronic lymphotic leukemia, acute lymphocytic leukemia (breast & bladder), acute myelogenous leukemia, meningeal leukemia, chronic myelogenous leukemia, and erythroleukemia. More commonly, the cancers treated include leukemia and B-cell cancers (e.g. lymphoma, multiple myeloma, and MDS.

Non-limiting examples of autoimmune diseases that can be treated using any herein described compound and methods of the disclosure include rheumatoid arthritis, psoriatic arthritis, juvenile idiopathic arthritis, multiple sclerosis, systemic lupus erythematosus, myasthenia gravis, juvenile onset diabetes, glomerulonephritis, autoimmune thyroiditis, Behcet's disease, Crohn's disease, ulcerative colitis, bullous pemphigoid, sarcoidosis, psoriasis, ichthyosis, Graves ophthalmopathy, psoriasis, psoriasis inflammatory bowel disease, and asthma.

As discussed in more detail herein, some embodiments also provide methods for treating and/or prevention various inflammatory disorders, diseases and conditions. Such inflammatory disorders, diseases and conditions include, without limitation, systemic autoimmune diseases such as, for example, lupus erythematosus, rheumatoid arthritis, multiple sclerosis, and psoriasis; and organ specific autoimmune diseases such as, for example, ulcerative colitis, myasthenia gravis, Grave's disease, Hashimoto's thyroiditis, Crohn's disease, lupus nephritis, autoimmune hemolytic anemias, immune thrombocytopenic purpura (ITP), thrombotic thrombocytopenic purpura (TTP), insulin dependent diabetes mellitus, glomerulonephritis, and rheumatic fever. Other inflammatory diseases that may be treated in accordance with this disclosure include, without limitation, other inflammatory arthritic conditions such as psoriatic arthritis, osteoarthritis and gouty arthritis, as well as other inflammatory conditions such as conjunctivitis, dermatitis, bronchitis, rhinitis etc., brought about by injury, allergies, infections, microorganisms, trauma, or physical or chemical agents. The treatment of inflammatory aspects of asthma, Sjogrens' syndrome, meningitis, adrenoleukodystrophy, CNS vasculitis, mitochondrial myopathies, Amyotrophic Lateral Sclerosis, Alzheimer's disease, or tumors is also contemplated as part of this disclosure. Examples of mitochondrial myopathies include MELAS syndrome, MERF syndrome, Leber's disease, Wernicke's encephalopathy, Rett syndrome, homocystinuria, hyperprolinemia, nonketotic hyperglycinemia, hydroxybutyric aminoaciduria, sulfite oxidase deficiency, and combined systems disease (B12 deficiency). In association with such prevention and/or treatment, articles of manufacture, compositions, methods of use, and medical treatments by the compounds described herein are also provided.

In some cases, it may be appropriate to administer any herein described compound as a salt. Examples of pharmaceutically acceptable salts include organic acid addition salts formed with acids which form a physiological acceptable anion, for example, tosylate, methanesulfonate, acetate, citrate, malonate, tartarate, succinate, benzoate, ascorbate, ketoglutarate, and glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example by reacting any herein described compound with a suitable base affording a physiologically acceptable anion. Alkali metal (for example, sodium, potassium or lithium) or alkaline earth metal (for example calcium) salts of carboxylic acids can also be made.

Any tablets, troches, pills, capsules, and the like, which incorporate any herein described compound, may also contain binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When there is a unit dosage form of any herein described compound, it may contain, in addition to materials of the herein type, a liquid carrier, such as a vegetable oil or a polyethylene glycol. Various other materials may be as coatings or to otherwise modify the physical form of a solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form should be pharmaceutically acceptable and substantially non-toxic in the amounts employed. In addition, any herein described compound may be incorporated into sustained-release preparations and devices.

Any herein described compound may also be administered intravenously or intraperitoneally by infusion or injection. Solutions of any herein described compound may be prepared in water, optionally mixed with a nontoxic surfactant. Dispersions may also be prepared in glycerol, liquid polyethylene glycols, triacetin, and mixtures thereof and in oils. Under ordinary conditions of storage and use, these preparations may contain a preservative to prevent the growth of microorganisms.

Sterile injectable solutions can be prepared by incorporating any herein described compound of in the sufficient therapeutic amount in the appropriate solvent with various of the other ingredients enumerated herein, as required, followed by filter sterilization. In the case of sterile powders for the preparation of sterile injectable solutions, the methods of preparation are vacuum drying and the freeze drying techniques, which yield a powder of the active ingredient plus any additional desired ingredient in the previously sterile-filtered solutions.

For topical administration, any herein described compound may be applied in pure form, i.e., when it is a liquid. However, it will generally be desirable to administer it to the skin as compositions or formulations, in combination with a dermatologically acceptable carrier, which may be a solid or a liquid. Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants and additional antimicrobial agents can be added to optimize the properties for a given use.

The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user, as known to those having ordinary skill in the art.

The disclosure also provides a pharmaceutical composition of the compounds described herein, or a pharmaceutically acceptable salt thereof, in combination with a pharmaceutically acceptable diluent or carrier. Further, the disclosure provides the use of compounds disclosed herein in combination with other known anti-inflammatory compounds.

In various embodiments, the disclosure provides a method for treating inflammatory disease and/or a condition associated with inflammation by administering to a mammal in need of such therapy, an effective amount of the compounds described herein, the compounds described herein in combination with an additional anti-inflammatory compound or a pharmaceutically acceptable salt thereof. In other embodiments, methods for the prevention of inflammatory disease and/or a condition associated with inflammation or a method for reducing the likelihood that a patient will develop such inflammation is provided. The methods can include administering to a mammal in need of such therapy, an effective amount of the compounds described herein or a pharmaceutically acceptable salt thereof.

There are also provided methods for treating a mammalian subject, particularly a human, suspected of having, or being prone to a disease or condition involving inflammation, by administering to a mammalian subject in need thereof a therapeutically effective amount of a compound of Formula I, or a pharmaceutically acceptable salt, solvate, or prodrug thereof, so as to affect treat or prevent inflammation.

In some embodiments, the methods for treating inflammation or preventing inflammation include administration of an effective amount of another therapeutic agent useful for treating or preventing the diseases or disorders disclosed herein. In some embodiments, the time in which the therapeutic effect of the other therapeutic agent is exerted overlaps with the time in which the therapeutic effect of the apogossypol or derivative is exerted.

In some embodiments, the other therapeutic agent is an anti-inflammatory agent. Examples of anti-inflammatory agents suitable for use according to some embodiments disclosed herein include, but are not limited to, steroids (e.g., cortisol, cortisone, fludrocortisone, prednisone, methylprednisolone, 6-methylprednisone, triamcinolone, betamethasone or dexamethasone), nonsteroidal anti-inflammatory drugs (NSAIDS (e.g., aspirin, acetaminophen, tolmetin, salicylates, ibuprofen, mefenamic acid, piroxicam, nabumetone, rofecoxib, celecoxib, etodolac or nimesulide). For the treatment of lupus erythmatosus, for example, the compounds disclosed herein may also be administered in conjunction with anti-malarial drugs including, for example, hydroxychloroquinone or in conjunction with cytotoxic chemotherapies including, for example, azathioprine and cyclophosphamide.

In some embodiments, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine).

Another type of therapeutic agent useful in the combination treatment of the disclosure is an antibody such as a humanized monoclonal antibody. Non-limiting examples include, the anti-CD99 antibody. See, for example, U.S. Pat. No. 7,223,395; White et al., Annu. Rev. Med., 52:125 (2001). Rituximab (Rituxan®; Genentech, South San Francisco, Calif.) is another therapeutic agent that is useful in a conjugate of the disclosure for treating rheumatoid arthritis. Another therapeutic agent useful in the disclosure also can be cytotoxic agents, which, as used herein, is any molecule that directly or indirectly promotes cell death. Specific anticancer agents include Flavopiridol, Adriamycin (doxorubicin), VP16 (Etoposide), Taxol (paclitaxel), cisplatin and the like.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, a-ketoglutarate, and a.-glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds useful in practicing the disclosure can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

The compounds may be systemically administered, e.g., orally, in combination with a pharmaceutically acceptable vehicle such as an inert diluent or an assimilable edible carrier. The route of administration is oral or intravenous. Other routes of administration include, for example, parental, intramuscular, topical and subcutaneous. The compounds may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The compound of Formula I may be administered in a variety of ways. For example, the tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the herein type, a liquid carrier, such as a vegetable oil or a polyethylene glycol. Various other materials may be as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The compounds may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders by the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium including, for example, water, ethanol, a polyol (for example, glycerol, propylene glycol, liquid polyethylene glycols, and the like), vegetable oils, nontoxic glyceryl esters, and suitable mixtures thereof The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be advisable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated herein, as required, followed by filter sterilization. In the case of sterile powders for the preparation of sterile injectable solutions, the methods of preparation are vacuum drying and the freeze drying techniques, which yield a powder of the active ingredient plus any additional desired ingredient in the previously sterile-filtered solutions.

For topical administration, the compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compound of Formula I to the skin are known in the art; for example, see U.S. Pat. Nos. 4,608,392, 4,992,478, 4,559,157, and 4,820,508.

Useful dosages of the compounds can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compounds of the compound of Formula 1 in a liquid composition, such as a lotion, may be between about 0.1 and about 25.0 mass %, such as between about 0.5 about 10.0 mass %. The concentration in a semi-solid or solid composition such as a gel or a powder may be between about 0.1 and about 5.0 mass %, such as between about 0.5 and 2.5 mass %.

The amount of the compound, or an active salt or derivative thereof, required for use in treatment will vary with the particular salt selected but also with the route of administration, the nature of the condition being treated and the age and condition of the patient and will be ultimately at the discretion of the attendant physician or clinician. In general, however, a suitable dose may be in the range of between about 0.2 and about 100.0 µmol/kg per day. In one embodiment, the dose can be, e.g., between about 0.2 to about 1.0 µmol/kg per day. In some embodiments, a suitable does may be in the rage of between about 0.5 and about 100 mg/kg, e.g., between about 10 and about 75 mg/kg of body weight per day, such as between about 3 and about 50 mg per kilogram body weight of the recipient per day, for example, in the range of between about 6 and about 90 mg/kg/day, such as in the range of between about 15 and about 60 mg/kg/day.

Pharmaceutical compositions suitable for use in the methods disclosed herein include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions disclosed herein can be chosen by the individual physician in view of the patient's condition. Typically, the dose range of the composition administered to the patient can be between about 0.5 and about 1000 mg/kg of the patient's body weight, or between about 1 and about 500 mg/kg, or between about 10 and about 500 mg/kg, or between about 50 and about 100 mg/kg of the patient's body weight. The dosage may be a single one or a series of two or more given in the course of one or more days, as is needed by the patient. Where no human dosage is established, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between about 0.1 mg and about 500 mg of each ingredient, such as between about 1 mg and about 250 mg, e.g. between about 5 and about 200 mg or an intravenous, subcutaneous, or intramuscular dose of each ingredient between about 0.01 mg and about 100 mg, such as between about 0.1 mg and about 60 mg, e.g. between about 1 and about 40 mg of each ingredient of the pharmaceutical compositions disclosed herein or a pharmaceutically acceptable salt thereof calculated as the free base, the composition being administered 1 to 4 times per day. Alternatively the compositions disclosed herein may be administered by continuous intravenous infusion, at a dose of each ingredient up to 400 mg per day. Thus, the total daily dosage by oral administration of each ingredient will typically be in the range between about 1 and about 2000 mg and the total daily dosage by parenteral administration will typically be in the range between about 0.1 and about 400 mg. In some embodiments, the compounds will be administered for a period of continuous therapy, for example for a week or more, or for months or years.

Dosage amount and interval may be adjusted individually to provide plasma levels of the active moiety, which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen, which maintains plasma levels above the MEC for 10-90% of the time, such as between 30-90%, e.g., between 50-90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

In various embodiments, the compositions may, if desired, be ed in a pack or dispenser device, which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions including a compound disclosed herein formulated in a compatible pharmaceutical carrier may also be prepared, placed in an appropriate container, and labeled for treatment of an indicated condition.

In various embodiments, compounds of the disclosure can be labeled using methods known in the art. One detectable group is a fluorescent group. Fluorescent groups typically produce a high signal to noise ratio, thereby providing increased resolution and sensitivity in a detection procedure. For example, the fluorescent group absorbs light with a wavelength above about 300 nm, such as above about 350 nm, e.g., above about 400 nm. The wavelength of the light emitted by the fluorescent group is above about 310 nm, such as above about 360 nm, e.g., above about 410 nm.

The fluorescent detectable moiety can be selected from a variety of structural classes, including the following non-limiting examples: 1- and 2-amino-naphthalene, p,p'diaminostilbenes, pyrenes, quaternary phenanthridine salts, 9-aminoacridines, p,p'-diaminobenzophenone imines, anthracenes, oxacarbocyanine, marocyanine, 3-aminoequilenin, perylene, bisbenzoxazole, bis-p-oxazolyl benzene, 1,2-benzophenazin, retinol, bis-3-aminopridinium salts, hellebrigenin, tetracycline, sterophenol, benzimidazolyl phenylamine, 2-oxo-3-chromen, indole, xanthen, 7-hydroxycoumarin, phenoxazine, salicylate, strophanthidin, porphyrins, triarylmethanes, flavin, xanthene dyes (e.g., fluorescein and rhodamine dyes); cyanine dyes; 4,4-difluoro-4-bora-3a,4a-diaza-s-indacene dyes and fluorescent proteins (e.g., green fluorescent protein, phycobiliprotein).

In various embodiments, the compounds can be labeled, where the labeling group spontaneously emits a signal, or generates a signal upon the introduction of a suitable stimulus. Labels, include atoms such as, for example, $^{13}C$, $^{15}N$, $^{19}F$, $^{1}H$ and the like. In various embodiments, the compound can be conveniently administered in unit dosage form; for example, containing between about 5 and about 1,000 mg, such as between about 10 and about 750 mg, e.g., between about 50 and about 500 mg of active ingredient per unit dosage form.

In some embodiments, the active ingredient can be administered to achieve peak plasma concentrations of the active compound of between about 0.5 and about 75 µM, such as between about 1 and about 50 µM, e.g., between about 2 and about 30 µM. This may be achieved, for example, by the intravenous injection of a 0.05 to 5% solution of the active ingredient, optionally in saline, or orally administered as a bolus containing about 1-100 mg of the active ingredient. Desirable blood levels can be maintained by, for example, continuous infusion to provide about 0.01-5.0 mg/kg/hr or by intermittent infusions containing about 0.4-15 mg/kg of the active ingredient(s).

The desired dose may conveniently be provided in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

EXAMPLES

Some aspects of the disclosure can be further illustrated by the following non-limiting examples.

Abbreviations: Bcl-2: B-cell lymphoma/leukemia-2; EDCI: 1-ethyl-3-(3'-dimethylaminopropyl)carbodiimide; 1D-$^{1}H$ NMR: one-dimensional $^{1}H$ nuclear magnetic resonance spectroscopy; SAR: Structure-activity relationship; FPA: Fluorescence Polarization Assays; ITC: Isothermal Titration Calorimetry; WT: Wild type; MEF: Mouse embryonic fibroblast cells; DKO: Bax/Bak Double knockout; MEF/DKO: Bax/Bak Double knockout mouse embryonic fibroblast cells; ACN: Acetonitrile; LC-MS: Liquid chromatography and tandem mass spectrometry; HPLC: High-performance liquid chromatography; TROSY: Transverse Relaxation-Optimized Spectroscopy; ADME: Absorption, Distribution, Metabolism, and Excretion; DMSO: Dimethyl sulphoxide; PAMPA: Parallel artificial membrane permeation assay; FITC: Fluorescein isothiocyanate; GST: Glutathione-S-transferase; PBS: Phosphate-buffered saline; SE: Standard error; PI: Propidium iodide; NADPH: Nicotinamide adenine dinucleotide phosphate; and Rpm: Rotations Per Minute.

Example 1

General Synthetic Procedures

Unless otherwise indicated, all reagents and anhydrous solvents ($CH_2Cl_2$, THF, diethyl ether, etc) were obtained from commercial sources and used without purification. All reactions were performed in oven-dried glassware. All reactions involving air or moisture sensitive reagents were performed under a nitrogen atmosphere. Silica gel or reverse phase chromatography was performed using prepacked silica gel or C-18 cartridges (RediSep), respectively. All final compounds were purified to >95% purity, as determined by a HPLC Breeze from Waters Co. using an Atlantis T3 3 µM 4.6 mm×150 mm reverse phase column. Compounds 11-14 were isolated using a CHIRALCEL OD-RH 5 μM 250 mm×10 mm reverse phase chiral column and the enantiomeric purity of compounds 11-14 was analyzed using a CHIRALCEL OD-RH 5 μM 250 mm×4.6 mm reverse phase chiral column on a HPLC from Water Corp. The eluant was a linear gradient with a flow rate of 5 mL/min for preparative and 1 mL/min for analytical column, respectively, from 60% A and 40% B to 20% A and 80% B in 15 min followed by 5 min at 100% B (Solvent A: $H_2O$ with 0.1% TFA; Solvent B: ACN with 0.1% TFA). Compounds were detected at λ=254 nm. $^1$H NMR spectra were recorded on Bruker 600 MHz instruments. Chemical shifts are reported in ppm (δ) relative to $^1$H ($Me_4Si$ at 0.00 ppm). Coupling constant (J) are reported in Hz throughout. Mass spectral data were acquired on Shimadzu LCMS-2010EV for low resolution, and on an Agilent ESI-TOF for high resolution.

Compound 1 is commercially available from Yixin Pharmaceutical Co. HPLC purity 99.0%, $t_R$=12.50 min and synthesis of compounds 2, 4, 5 and 6 have been previously reported.[20]

Example 2

Synthesis of 1,1',6,6',7,7'-Hexamethoxy-3,3'-dimethyl-$N^5$,$N^{5'}$-bis(2-phenylpropyl)-2,2'-binaphthyl-5,5'-dicarboxamide (7)

Compound 6 (1.35 g, 2.45 mmol), EDCI (1.30 g, 6.76 mmol) and HOBT (910 mg, 6.76 mmol) were dissolved in 30 mL of dry $CH_2Cl_2$ and stirred at room temperature for 15 min under nitrogen atmosphere. (R)-β-methylphenethylamine (0.81 mL, 5.63 mmol) and N,N-diisopropylethylamine (1.7 mL, 9.8 mmol) were added and the reaction mixture was stirred at room temperature for 20 h. The mixture was then poured onto 100 mL of water and the solution was extracted with $CH_2Cl_2$ (3×100 mL). The ether extracts were washed with water and brine, dried over magnesium sulfate and filtered. Evaporation of the solvent in vacuo and the residue was purified by silica chromatography to give 1.46 g (76%) of compound 7 as a yellow solid. $^1$H NMR (600 MHz, $CD_3OD$) δ 7.36 (s, 2H), 7.33 (d, J=6.6 Hz, 4H), 7.32 (t, $J_1$=7.2 Hz, $J_2$=6.6 Hz, 4H), 7.21 (m, 4H), 4.59 (s, 4H), 3.98 (s, 6H), 3.85 (s, 6H), 3.76 (m, 2H), 3.63 (m, 2H), 3.54 (s, 3H), 3.53 (s, 3H), 2.01 (s, 3H), 2.00 (s, 3H), 1.38 (d, $J_1$=6.0 Hz, 6H). HRMS calcd for $C_{48}H_{52}N_2O_8$ 785.3796 (M+H), found 785.3790.

Example 3

Synthesis of 1,1',6,6',7,7'-Hexamethoxy-3,3'-dimethyl-$N^5$,$N^{5'}$-bis(2-phenylpropyl)-2,2'-binaphthyl-5,5'-dicarboxamide (8)

Compound 6 (1.0 g, 1.81 mmol), EDCI (960 mg, 5.0 mmol) and HOBT (181 mg, 1.34 mmol) were dissolved in 25 mL of dry $CH_2Cl_2$ and stirred at room temperature for 10 min under nitrogen atmosphere. (S)-β-methylphenethylamine (0.60 mL, 4.17 mmol) and N,N-diisopropylethylamine (1.26 mL, 7.3 mmol) were added and the reaction mixture was stirred at room temperature for 24 h. The mixture was then poured onto 50 mL of water and the solution was extracted with $CH_2Cl_2$ (3×100 mL). The ether extracts were washed with water and brine, dried over magnesium sulfate and filtered. Evaporation of the solvent in vacuo and the residue was purified by silica chromatography to give 0.87 g (60%) of compound 8 as a yellow solid. $^1$H NMR (600 MHz, $CD_3OD$) δ (600 MHz, $CD_3OD$) δ 7.48 (s, 2H), 7.36 (d, J=6.0 Hz, 4H), 7.32 (t, $J_1$=7.2 Hz, $J_2$=7.2 Hz, 4H), 7.22 (m, 4H), 4.59 (s, 4H), 3.98 (s, 6H), 3.84 (s, 6H), 3.76 (m, 2H), 3.63 (m, 2H), 3.54 (s, 3H), 3.53 (s, 3H), 2.01 (s, 3H), 1.99 (s, 3H), 1.38 (d, $J_1$=6.6 Hz, 6H). HRMS calcd for $C_{48}H_{52}N_2O_8$ 785.3796 (M+H), found 785.3788.

Example 4

Synthesis of 1,1',6,6',7,7'-Hexahydroxy-3,3'-dimethyl-$N^5$,$N^{5'}$-bis(2-phenylpropyl)-2,2'-binaphthyl-5,5'-dicarboxamide (9)

0.65 mL of $BBr_3$ solution (1.72 g, 6.85 mmol) was added dropwise into a solution of compound 7 (420 mg, 0.55 mmol) in 20 mL of anhydrous $CH_2Cl_2$ at −78° C. Stirring was continued at −78° C. for 1 h, 0° C. for 1 h, and ambient temperature for 1 h. 50 grams of ice containing 10 mL of 6M HCl was added to the mixture and stirred for 30 min at room temperature. The aqueous layer was extracted with ethyl acetate (3×60 mL). The combined organic layer was washed with water, brine and dried over $MgSO_4$. The solvent was concentrated in vacuo and the residue was purified using C-18 column chromatography followed by preparative HPLC ($H_2O$/Acetonitrile) to give 150 mg of compound 9 (39%) as white-yellow solid. $^1$H NMR (600 MHz, $CD_3OD$) δ 7.39 (d, J=4.2 Hz, 2H), 7.19 (m, 4H), 7.15 (t, $J_1$=6.0 Hz, $J_2$=6.0 Hz, 4H), 7.03 (t, $J_1$=6.0 Hz, $J_2$=6.0 Hz, 2H), 6.89 (s, 1H), 6.81 (s, 1H), 3.49 (m, 4H), 3.02 (m, 2H), 1.72 (s, 3H), 1.71 (s, 3H), 1.25 (s, 3H), 1.24 (s, 3H). HRMS calcd for $C_{42}H_{40}N_2O_8$ 701.2857 (M+H), found 701.2865. 100 mg of compound 9 was further purified using a CHIRALCEL OD-RH 5 μM 250 mm×10 mm reverse phase chiral column to give 25 mg of compound 11 and 28 mg of compound 12, respectively.

Example 5

Synthesis of (S)-1,1',6,6',7,7'-hexahydroxy-3,3'-dimethyl-$N^5$—(R)-2-phenylpropyl)-$N^{5'}$—((R)-2-phenylpropyl)-2,2'-binaphthyl-5,5'-dicarboxamide (11)

$^1$H NMR (600 MHz, $CD_3OD$) δ 7.57 (s, 2H), 7.37 (d, J=7.8 Hz, 4H), 7.33 (t, $J_1$=7.2 Hz, $J_2$=7.8 Hz, 4H), 7.22 (t, $J_1$=$J_2$=7.2 Hz, 2H), 7.07 (s, 2H), 3.67 (m, 4H), 3.23 (m, 2H), 1.90 (s, 6H), 1.43 (d, J=7.2 Hz, 6H). $^{13}$C NMR (600 MHz, $CD_3OD$) δ 169.73, 149.20, 144.64, 143.95, 133.86, 128.15, 127.17, 126.95, 126.10, 118.38, 116.60, 115.20, 114.37, 105.57, 46.40, 39.56, 19.33, 18.58. HPLC purity 99.0%, $t_R$=9.13 min. Enantiomeric purity 99.7%, $t_R$=12.35 min. HRMS calcd for $C_{42}H_{40}N_2O_8$ 701.2857 (M+H), found 701.2854.

Example 6

Synthesis of (R)-1,1',6,6',7,7'-hexahydroxy-3,3'-dimethyl-$N^5$—(R)-2-phenylpropyl)-$N^{5'}$—((R)-2-phenylpropyl)-2,2'-binaphthyl-5,5'-dicarboxamide (12)

$^1$H NMR (600 MHz, $CD_3OD$) δ 7.57 (s, 2H), 7.38 (d, J=7.8 Hz, 4H), 7.33 (t, $J_1$=7.2 Hz, $J_2$=7.8 Hz, 4H), 7.22 (t, $J_1$=$J_2$=7.2 Hz, 2H), 6.99 (s, 2H), 3.75 (dd, $J_1$=7.2 Hz, $J_2$=13.2 Hz, 2H), 3.62 (dd, $J_1$=7.2 Hz, $J_2$=13.2 Hz, 2H), 3.20 (m, 2H), 1.89 (s, 6H), 1.42 (d, J=6.6 Hz, 6H). $^{13}$C NMR (600 MHz, $CD_3OD$) δ 169.67, 149.18, 144.62, 144.54, 143.92, 133.85, 128.14, 127.16, 126.97, 126.12, 118.36, 116.59, 115.14, 114.35, 105.56, 46.34, 39.66, 19.63, 18.78. HPLC purity 99.0%, $t_R$=9.30 min. Enantiomeric purity 99.5%, $t_R$=10.28 min. HRMS calcd for $C_{42}H_{40}N_2O_8$ 701.2857 (M+H), found 701.2848.

Example 7

Synthesis of 1,1',6,6',7,7'-Hexahydroxy-3,3'-dimethyl-$N^5$,$N^{5'}$-bis(2-phenylpropyl)-2,2'-binaphthyl-5,5'-dicarboxamide (10)

0.45 mL of $BBr_3$ solution (1.18 g, 4.73 mmol) was added dropwise into a solution of compound 8 (310 mg, 0.40 mmol) in 20 mL of anhydrous $CH_2Cl_2$ at −78° C. Stirring was continued at −78° C. for 1 h, 0° C. for 1 h, and ambient temperature for 1 h. 50 grams of ice containing 10 mL of 6M HCl was added to the mixture and stirred for 1 h at room temperature. The aqueous layer was extracted with dichloromethane (3×50 mL). The combined organic layer was washed with water, brine and dried over $MgSO_4$. The solvent was concentrated in vacuo and the residue was purified using C-18 column chromatography ($H_2O$/Acetonitrile) to give 200 mg of compound 10 (72%) as white-yellow solid. $^1H$ NMR (600 MHz, $CD_3OD$) δ 7.56 (d, J=6.6 Hz, 2H), 7.39 (t, $J_1$=6.0 Hz, $J_2$=3.0 Hz, 4H), 7.35 (t, $J_1$=6.0 Hz, $J_2$=6.6 Hz, 4H), 7.23 (t, $J_1$=6.0 Hz, $J_2$=6.6 Hz, 2H), 7.06 (s, 1H), 6.99 (s, 1H), 3.76 (dd, $J_1$=6.6 Hz, $J_2$=11.4 Hz, 1H), 3.68 (m, 3H), 3.22 (m, 2H), 1.90 (s, 3H), 1.89 (s, 3H), 1.43 (m, 6H). HRMS calcd for $C_{42}H_{40}N_2O_8$ 701.2857 (M+H), found 701.2853. 150 mg of compound 10 was further purified using a CHIRALCEL OD-RH 5 µM 250 mm×10 mm reverse phase chiral column to give 50 mg of compound 13 and 58 mg of compound 14, respectively.

Example 8

Synthesis of (S)-1,1',6,6',7,7'-hexahydroxy-3,3'-dimethyl-$N^5$—((S)-2-phenylpropyl)-$N^{5'}$—((S)-2-phenylpropyl)-2,2'-binaphthyl-5,5'-dicarboxamide (13)

$^1H$ NMR (600 MHz, $CD_3OD$) δ 7.57 (s, 2H), 7.38 (d, J=7.2 Hz, 4H), 7.33 (t, $J_1$=7.2 Hz, $J_2$=7.8 Hz, 4H), 7.22 (t, $J_1$=7.2 Hz, $J_2$=7.8 Hz, 2H), 6.99 (s, 2H), 3.75 (dd, $J_1$=7.8 Hz, $J_2$=13.2 Hz, 2H), 3.62 (dd, $J_1$=7.8 Hz, $J_2$=13.2 Hz, 2H), 3.20 (m, 2H), 1.89 (s, 6H), 1.40 (d, J=6.6 Hz, 6H). $^{13}C$ NMR (600 MHz, $CD_3OD$) δ 169.66, 149.17, 144.62, 144.54, 143.92, 133.85, 128.13, 127.16, 126.96, 126.11, 118.36, 116.60, 115.15, 114.34, 105.55, 46.33, 39.66, 19.35, 18.67. HPLC purity 99.4%, $t_R$=9.31 min. Enantiomeric purity 99.1%, $t_R$=12.38 min. HRMS calcd for $C_{42}H_{40}N_2O_8$ 701.2857 (M+H), found 701.2849.

Example 9

Synthesis of (R)-1,1',6,6',7,7'-hexahydroxy-3,3'-dimethyl-$N^5$—(S)-2-phenylpropyl)-$N^{5'}$—((S)-2-phenylpropyl)-2,2'-binaphthyl-5,5'-dicarboxamide (14).

$^1H$ NMR (600 MHz, $CD_3OD$) δ 7.57 (s, 2H), 7.37 (d, J=7.8 Hz, 3H), 7.33 (t, $J_1$=7.2 Hz, $J_2$=7.8 Hz, 4H), 7.22 (t, $J_1$=$J_2$=7.2 Hz, 2H), 7.06 (s, 2H), 3.66 (m, 4H), 3.22 (m, 2H), 1.90 (s, 6H), 1.40 (s, J=6.6 Hz, 6H). $^{13}C$ NMR (600 MHz, $CD_3OD$) δ 169.71, 149.16, 14.64, 144.58, 144.03, 133.84, 128.15, 127.16, 126.95, 126.09, 118.41, 116.56 115.23, 114.41, 105.57, 46.40, 39.56, 19.34, 18.60. HPLC purity 98.6%, $t_R$=9.22 min. Enantiomeric purity 99.5%, $t_R$=10.57 min. HRMS calcd for $C_{42}H_{40}N_2O_8$ 701.2857 (M+H), found 701.2852.

Example 10

Molecular Modeling

Molecular modeling studies were conducted on a Linux workstation and a 64 3.2-GHz CPUs Linux cluster. Docking studies were performed using the crystal structure of Bcl-$X_L$ and Mcl-1 in complex with a BH3 mimetic ligand (Protein Data Bank code 2YXJ and 2NL9, respectively).[30, 32, 41, 42] The ligand was extracted from the protein structure and was used to define the binding site for small molecules. Compounds 11-14 were docked into the Bcl-2 family protein by the GOLD[43] docking program using GoldScore[44] as the scoring function. The active site radius was set at 10 Å and 10 GA solutions were generated for each molecule. The GA docking procedure in GOLD[43] allowed the small molecules to flexibly explore the best binding conformations whereas the protein structure was static. The protein surface was prepared with the program MOLCAD[45] as implemented in Sybyl (Tripos, St. Louis) and was used to analyze the binding poses for studied small molecules.

Example 11

Fluorescence Polarization Assays (FPAs)

A Bak BH3 peptide (F-BakBH3) (GQVGRQLAIIGD-DINR) was labeled at the N-terminus with fluorescein isothiocyanate (FITC) (Molecular Probes) and purified by HPLC. For competitive binding assays, 100 nM GST-Bcl-$X_L$ ΔTM protein was preincubated with the tested compound at varying concentrations in 47.5 µL PBS (pH=7.4) in 96-well black plates at room temperature for 10 min, then 2.5 µL of 100 nM FITC-labeled Bak BH3 peptide was added to produce a final volume of 50 µL. The wild-type and mutant Bak BH3 peptides were included in each assay plate as positive and negative controls, respectively. After 30 min incubation at room temperature, the polarization values in millipolarization units[46] were measured at excitation/emission wavelengths of 480/535 nm with a multilabel plate reader (PerkinElmer). $IC_{50}$ was determined by fitting the experimental data to a sigmoidal dose-response nonlinear regression model (SigmaPlot 10.0.1, Systat Software, Inc., San Jose, Calif., USA). Data reported are mean of three independent experiments±standard error (SE). Performance of Bcl-2 and Mcl-1 FPA are similar. Briefly, 50 nM of GST-Bcl-2 or -Mcl-1 were incubated with various concentrations of compound (4 and 11-14) for 2 min, then 15 nM FITC-conjugated-Bim BH3 peptide[47] was added in PBS buffer. Fluorescence polarization was measured after 10 min.

Example 12

Cell Viability and Apoptosis Assays

The activity of the compounds against human cancer cell lines (PC3, H460, H1299) were assessed by using the ATP-LITE assay (PerkinElmer). All cells were seeded in either 12F2 or RPMI1640 medium with 5 mM L-glutamine supplemented with 5% fetal bovine serum (Mediatech Inc.), penicillin and streptomycin (Omega). For maintenance, cells were cultured in 5% FBS. Cells plated into 96 well plates at varying initial densities depending on doubling time. H460 and H1299 plated at 2000 cells/well, and PC3 at 3000 cells/well. Compounds were diluted to final concentrations with 0.1% DMSO. Prior to dispensing compounds onto cells, fresh 5% media was placed into wells. Administration of compounds occurred 24 hours after seeding into the fresh media. Cell viability was evaluated using ATP-LITE reagent (PerkinElmer) after 72 hours of treatment. Data were normalized to the DMSO control-treated cells using Prism version 5.01 (Graphpad Software).

The apoptotic activity of the compounds against BP3 cells was assessed by staining with Annexin V- and propidium iodide (PI). BP3 cell line was cultured in RPMI 1640 medium (Mediatech Inc., Herndon, Va. 20171) containing 10% fetal bovine serum (Mediatech Inc., Herndon, Va. 20171) and Penicillin/Streptomycin (Mediatech Inc., Herndon, Va. 20171). Cells were cultured with various concentrations of compounds 4 and 11-14 for 1-2 days. The percentage of viable cells was determined by FITC-Annexin V- and propidium iodide (PI)-labeling, using an Apoptosis Detection kit (BioVision Inc.), and analyzing stained cells by flow cytometry (FACSort; Bectin-Dickinson, Inc.; Mountain View, Calif.). Cells that were annexin-V-negative and PI-negative were considered viable.

The apoptotic activity of compounds 4 and 11-14 against mouse embryonic fibroblast wild-type cells (MEF/WT) and mouse embryonic fibroblast BAX/Bak double knockout cells (DKO/MEF) was assessed by staining with Annexin V- and propidium iodide (PI). Wild-type MEF and DKO/MEF were seeded in 24-well plate at a seeding density of half a million per well (in 1 ml of DMEM medium supplemented by 10% FCS). Next day, compound was added to wild-type and DKO cells at final concentration of 0, 2.5, 5.0, 7.5, 10 and 30 µM. On the following day, floating cells were pooled with adherent cells harvested after brief incubation with 0.25% Trypsin/EDTA solution (Gibco/In-Vitrogen Inc.). Cells were centrifuged and supernatant was discarded, and cell pellet was re-suspended with 0.2 ml of Annexin-V binding buffer, followed by addition of 1 µl Annexin-FITC and 1 µl PI (propidium iodide). The percentage of viable cells was determined by a 3-color FACSort instrument and data analyzed by Flow-Jo program, scoring Annexin V-negative, PI-negative as viable cells.

Example 13

Bcl-2 Transgenic Mice Studies

Transgenic mice expressing Bcl-2 have been described as the B6 line.[48] The BCL-2 transgene represents a minigene version of a t(14;18) translocation in which the human BCL-2 gene is fused with the immunoglobulin heavy-chain (IgH) locus and associated IgH enhancer. The transgene was propagated on the Balb/c background. These mice develop polyclonal B-cell hyperplasia with asynchronous transformation to monoclonal aggressive lymphomas beginning at approximately 6 months of age, with approximately 90% of mice undergoing transformation by the age of 12 to 24 months. All animals used here had not yet developed aggressive lymphoma.

Example 14

Mouse Experiments

Compounds dissolved in 500 µL of solution (Ethanol: Cremophor EL: Saline=10:10:80) were injected intraperitoneally to two age- and sex-matched B6Bcl2 mouse, while control-mice were injected intraperitoneally with 500 µL of the same formulation without compound. After 24 hours, B6Bcl2 mice were sacrificed by intraperitoneal injection of lethal dose of Avertin. Spleen was removed and weighed. The spleen weight of mice is used as an end-point for assessing activity as we determined that spleen weight is highly consistent in age- and sex-matched Bcl-2-transgenic mice in preliminary studies.[17] Variability of spleen weight was within ±2% among control-treated age-matched, sex-matched B6Bcl2 mice.

Example 15

M2182 Cell Lines and Stable Clones

M2182 progressed prostate cancer cells were obtained from Dr. Joy Ware (Virginia Commonwealth University, School of Medicine, Richmond, Va.) and cultured as described.[37] M2182 is a tumorigenic but non-metastatic variant of normal prostate epithelial P69 cells. pGL3 basic plasmid (Promega) was used to transfect M2182 cells using Lipofectamine 2000 (Invitrogen) according to the manufacturer's protocol. Cells were then selected for 2 weeks in 200 µg/ml of hygromycin, and individual colonies were isolated, expanded, and maintained in 5 µg/ml hygromycin. The overexpression of luciferase in these clones was confirmed by measuring luciferase activity.

Example 16

Human Prostate Cancer Xenografts in Athymic Nude Mice

M2182-Luc cells ($1\times10^6$) were injected s.c. in 100 µL of PBS in the left and right flanks of male athymic nude mice ($NCR^{nu/nu}$, 4 weeks old, 20 g body weight) as described previously.[40] After establishing visible tumors of ~75-mm³, requiring ~5-6 days, compound dissolved in 500 µL of solvent (ethanol/Cremophor EL/saline=10:10:80) were injected intraperitoneally (i.p.). The injections were given every 2 days for a total of nine injections. Three treatment groups were established for the experiment of compound 4, i.e., DMSO only, 10 mg/kg and 25 mg/kg of compound 4. Four treatment groups were established for the experiment of compound 11, i.e., DMSO only, 1 mg/kg, 3 mg/kg and 5 mg/kg of compound 11. A minimum of five animals was used per experimental condition. For in vivo imaging of tumors, the mice were anesthetized and injected i.p. with 150 mg/kg luciferin and light emitted from each tumor was determined using a Xenogen system with CCD camera with an integration time of 1 min. Luminescence measurements were made using Living Image software (version 2.50.1; Xenogen). At the end of the experiment, the animals were sacrificed, and the tumors were removed and photographed.

REFERENCES

1. Vaux, D. L.; Korsmeyer, S. J. Cell death in development. *Cell* 1999, 96, 245-254.
2. Reed, J. C. Dysregulation of apoptosis in cancer. *J Clin Oncol* 1999, 17, 2941-2953.
3. Johnstone, R. W.; Ruefli, A. A.; Lowe, S. W. Apoptosis: a link between cancer genetics and chemotherapy. *Cell* 2002, 108, 153-164.
4. Reed, J. C. Apoptosis-based therapies. *Nature reviews Drug discovery* 2002, 1, 111-121.
5. Reed, J. C. Bcl-2 family proteins. *Oncogene* 1998, 17, 3225-3236.
6. Adams, J. M.; Cory, S. The Bcl-2 protein family: arbiters of cell survival. *Science* (New York, N.Y.) 1998, 281, 1322-1326.
7. Gross, A.; McDonnell, J. M.; Korsmeyer, S. J. BCL-2 family members and the mitochondria in apoptosis. *Genes & development* 1999, 13, 1899-1911.

8. Wang, J. L.; Liu, D.; Zhang, Z. J.; Shan, S.; Han, X.; Srinivasula, S. M.; Croce, C. M.; Alnemri, E. S.; Huang, Z. Structure-based discovery of an organic compound that binds Bcl-2 protein and induces apoptosis of tumor cells. *Proceedings of the National Academy of Sciences of the United States of America* 2000, 97, 7124-7129.
9. Degterev, A.; Lugovskoy, A.; Cardone, M.; Mulley, B.; Wagner, G.; Mitchison, T.; Yuan, J. Identification of small-molecule inhibitors of interaction between the BH3 domain and Bcl-xL. *Nat Cell Biol* 2001, 3, 173-182.
10. Reed, J. C. Bcl-2 family proteins: strategies for overcoming chemoresistance in cancer. *Advances in pharmacology* (San Diego, Calif.) 1997, 41, 501-532.
11. Kitada, S.; Leone, M.; Sareth, S.; Zhai, D.; Reed, J. C.; Pellecchia, M. Discovery, characterization, and structure-activity relationships studies of proapoptotic polyphenols targeting B-cell lymphocyte/leukemia-2 proteins. *Journal of medicinal chemistry* 2003, 46, 4259-4264.
12. Zhang, M.; Liu, H.; Guo, R.; Ling, Y.; Wu, X.; Li, B.; Roller, P. P.; Wang, S.; Yang, D. Molecular mechanism of gossypol-induced cell growth inhibition and cell death of HT-29 human colon carcinoma cells. *Biochemical pharmacology* 2003, 66, 93-103.
13. Wang, S.; Yang, D. Small Molecular Antagonists of Bcl-2 family proteins. US patent applications series no. 2004/0214902 A1, 2004.
14. Wang, G.; Nikolovska-Coleska, Z.; Yang, C.-Y.; Wang, R.; Tang, G.; Guo, J.; Shangary, S.; Qiu, S.; Gao, W.; Yang, D.; Meagher, J.; Stuckey, J.; Krajewski, K.; Jiang, S.; Roller, P. P.; Abaan, H. O.; Tomita, Y.; Wang, S. Structure-based design of potent small-molecule inhibitors of anti-apoptotic Bcl-2 proteins. *Journal of medicinal chemistry* 2006, 49, 6139-6142.
15. Mohammad, R. M.; Wang, S.; Aboukameel, A.; Chen, B.; Wu, X. Chen, J.; Al-Katib, A. Preclinical studies of a non-peptidic small-molecule inhibitor of Bcl-2 and Bcl-X(L) [(-)-gossypol] against diffuse large cell lymphoma. *Mol Cancer Ther* 2005, 4, 13-21.
16. Becattini, B.; Kitada, S.; Leone, M.; Monosov, E.; Chandler, S.; Zhai, D.; Kipps, T. J.; Reed, J. C.; Pellecchia, M. Rational design and real time, in-cell detection of the proapoptotic activity of a novel compound targeting Bcl-X(L). *Chemistry & biology* 2004, 11, 389-395.
17. Kitada, S.; Kress, C. L.; Krajewska, M.; Jia, L.; Pellecchia, M.; Reed, J. C. Bcl-2 antagonist apogossypol (NSC736630) displays single-agent activity in Bcl-2-transgenic mice and has superior efficacy with less toxicity compared with gossypol (NSC 19048). *Blood* 2008, 111, 3211-3219.
18. Coward, L.; Gorman, G.; Noker, P.; Kerstner-Wood, C.; Pellecchia, M.; Reed, J. C.; Jia, L. Quantitative determination of apogossypol, a pro-apoptotic analog of gossypol, in mouse plasma using LC/MS/MS. *Journal of pharmaceutical and biomedical analysis* 2006, 42, 581-586.
19. Wei, J.; Rega, M. F.; Kitada, S.; Yuan, H.; Zhai, D.; Risbood, P.; Seltzman, H. H.; Twine, C. E.; Reed, J. C.; Pellecchia, M. Synthesis and evaluation of Apogossypol atropisomers as potential Bcl-xL antagonists. *Cancer Lett* 2009, 273, 107-113.
20. Wei, J.; Kitada, S.; Rega, M. F.; Stebbins, J. L.; Zhai, D.; Cellitti, J.; Yuan, H.; Emdadi, A.; Dahl, R.; Zhang, Z.; Yang, L.; Reed, J. C.; Pellecchia, M. Apogossypol derivatives as pan-active inhibitors of antiapoptotic B-cell lymphoma/leukemia-2 (Bcl-2) family proteins. *Journal of medicinal chemistry* 2009, 52, 4511-4523.
21. Wei, J.; Kitada, S.; Rega, M. F.; Emdadi, A.; Yuan, H.; Cellitti, J.; Stebbins, J. L.; Zhai, D.; Sun, J.; Yang, L.; Dahl, R.; Zhang, Z.; Wu, B.; Wang, S.; Reed, T. A.; Lawrence, N.; Sebti, S.; Reed, J. C.; Pellecchia, M. Apogossypol derivatives as antagonists of antiapoptotic Bcl-2 family proteins. *Mol Cancer Ther* 2009, 8, 904-913.
22. Yamanoi, Y.; Nishihara, H. Direct and selective arylation of tertiary silanes with rhodium catalyst. *J Org Chem* 2008, 73, 6671-6678.
23. Royer, R. E.; Deck, L. M.; Vander Jagt, T. J.; Martinez, F. J.; Mills, R. G.; Young, S. A.; Vander Jagt, D. L. Synthesis and anti-HIV activity of 1,1'-dideoxygossypol and related compounds. *J Med Chem* 1995, 38, 2427-2432.
24. Rega, M. F.; Leone, M.; Jung, D.; Cotton, N. J.; Stebbins, J. L.; Pellecchia, M. Structure-based discovery of a new class of Bcl-xL antagonists. *Bioorg Chem* 2007, 35, 344-353.
25. Wesarg, E.; Hoffarth, S.; Wiewrodt, R.; Kroll, M.; Biesterfeld, S.; Huber, C.; Schuler, M. Targeting BCL-2 family proteins to overcome drug resistance in non-small cell lung cancer. *Int J Cancer* 2007, 121, 2387-2394.
26. Brien, G.; Trescol-Biemont, M. C.; Bonnefoy-Berard, N. Downregulation of Bfl-1 protein expression sensitizes malignant B cells to apoptosis. *Oncogene* 2007, 26, 5828-32.
27. Li, J.; Viallet, J.; Haura, E. B. A small molecule pan-Bcl-2 family inhibitor, GX15-070, induces apoptosis and enhances cisplatin-induced apoptosis in non-small cell lung cancer cells. *Cancer Chemother Pharmacol* 2008, 61, 525-534.
28. Voortman, J.; Checinska, A.; Giaccone, G.; Rodriguez, J. A.; Kruyt, F. A. Bortezomib, but not cisplatin, induces mitochondria-dependent apoptosis accompanied by up-regulation of noxa in the non-small cell lung cancer cell line NCI-H460. *Mol Cancer Ther* 2007, 6, 1046-1053.
29. Ferreira, C. G.; Span, S. W.; Peters, G. J.; Kruyt, F. A.; Giaccone, G. Chemotherapy triggers apoptosis in a caspase-8-dependent and mitochondria-controlled manner in the non-small cell lung cancer cell line NCI-H460. *Cancer Res* 2000, 60, 7133-7141.
30. Lee, E. F.; Czabotar, P. E.; Smith, B. J.; Deshayes, K.; Zobel, K.; Colman, P. M.; Fairlie, W. D. Crystal structure of ABT-737 complexed with Bcl-xL: implications for selectivity of antagonists of the Bcl-2 family. *Cell death and differentiation* 2007, 14, 1711-1713.
31. Zhang, H.; Cowan-Jacob, S. W.; Simonen, M.; Greenhalf, W.; Heim, J.; Meyhack, B. Structural basis of BFL-1 for its interaction with BAX and its anti-apoptotic action in mammalian and yeast cells. *J Biol Chem* 2000, 275, 11092-11099.
32. Oltersdorf, T.; Elmore, S. W.; Shoemaker, A. R.; Armstrong, R. C.; Augeri, D. J.; Belli, B. A.; Bruncko, M.; Deckwerth, T. L.; Dinges, J.; Hajduk, P. J.; Joseph, M. K.; Kitada, S.; Korsmeyer, S. J.; Kunzer, A. R.; Letai, A.; Li, C.; Mitten, M. J.; Nettesheim, D. G.; Ng, S.; Nimmer, P. M.; O'Connor, J. M.; Oleksijew, A.; Petros, A. M.; Reed, J. C.; Shen, W.; Tahir, S. K.; Thompson, C. B.; Tomaselli, K. J.; Wang, B.; Wendt, M. D.; Zhang, H.; Fesik, S. W.; Rosenberg, S. H. An inhibitor of Bcl-2 family proteins induces regression of solid tumours. *Nature* 2005, 435, 677-681.
33. Cory, S.; Adams, J. M. Killing cancer cells by flipping the Bcl-2/Bax switch. *Cancer cell* 2005, 8, 5-6.
34. Wei, M. C.; Zong, W. X.; Cheng, E. H.; Lindsten, T.; Panoutsakopoulou, V.; Ross, A. J.; Roth, K. A.; MacGregor, G. R.; Thompson, C. B.; Korsmeyer, S. J. Proapoptotic BAX and BAK: a requisite gateway to mitochondrial dysfunction and death. *Science* (New York, N.Y.) 2001, 292, 727-730.

35. Vogler, M.; Weber, K.; Dinsdale, D.; Schmitz, I.; Schulze-Osthoff, K.; Dyer, M. J.; Cohen, G. M. Different forms of cell death induced by putative BCL2 inhibitors. *Cell Death Differ* 2009. 16, 1030-1039.
36. van de Donk, N. W.; Kamphuis, M. M.; van Dijk, M.; Borst, H. P.; Bloem, A. C.; Lokhorst, H. M. Chemosensitization of myeloma plasma cells by an antisense-mediated downregulation of Bcl-2 protein. *Leukemia* 2003, 17, 211-219.
37. Lebedeva, I. V.; Sarkar, D.; Su, Z. Z.; Kitada, S.; Dent, P.; Stein, C. A.; Reed, J. C.; Fisher, P. B. Bcl-2 and Bcl-x(L) differentially protect human prostate cancer cells from induction of apoptosis by melanoma differentiation associated gene-7, mda-7/IL-24. *Oncogene* 2003, 22, 8758-8773.
38. Bae, V. L.; Jackson-Cook, C. K.; Maygarden, S. J.; Plymate, S. R.; Chen, J.; Ware, J. L. Metastatic sublines of an SV40 large T antigen immortalized human prostate epithelial cell line. *Prostate* 1998, 34, 275-282.
39. Sarkar, D.; Su, Z. Z.; Vozhilla, N.; Park, E. S.; Gupta, P.; Fisher, P. B. Dual cancer-specific targeting strategy cures primary and distant breast carcinomas in nude mice. *Proc Natl Acad Sci USA* 2005, 102, 14034-14039.
40. Su, Z. Z.; Sarkar, D.; Emdad, L.; Duigou, G. J.; Young, C. S.; Ware, J.; Randolph, A.; Valerie, K.; Fisher, P. B. Targeting gene expression selectively in cancer cells by using the progression-elevated gene-3 promoter. *Proc Natl Acad Sci USA* 2005, 102, 1059-1064.
41. Bruncko, M.; Oost, T. K.; Belli, B. A.; Ding, H.; Joseph, M. K.; Kunzer, A.; Martineau, D.; McClellan, W. J.; Mitten, M.; Ng, S. C.; Nimmer, P. M.; Oltersdorf, T.; Park, C. M.; Petros, A. M.; Shoemaker, A. R.; Song, X.; Wang, X.; Wendt, M. D.; Zhang, H.; Fesik, S. W.; Rosenberg, S. H.; Elmore, S. W. Studies leading to potent, dual inhibitors of Bcl-2 and Bcl-xL. *J Med Chem* 2007, 50, 641-662.
42. Czabotar, P. E.; Lee, E. F.; van Delft, M. F.; Day, C. L.; Smith, B. J.; Huang, D. C. S.; Fairlie, W. D.; Hinds, M. G.; Colman, P. M. Structural insights into the degradation of Mcl-1 induced by BH3 domains. *Proceedings of the National Academy of Sciences of the United States of America* 2007, 104, 6217-6222.
43. Jones, G.; Willett, P.; Glen, R. C.; Leach, A. R.; Taylor, R. Development and validation of a genetic algorithm for flexible docking. *Journal of molecular biology* 1997, 267, 727-748.
44. Eldridge, M. D.; Murray, C. W.; Auton, T. R.; Paolini, G. V.; Mee, R. P. Empirical scoring functions: I. The development of a fast empirical scoring function to estimate the binding affinity of ligands in receptor complexes. *J Comput Aided Mol Des* 1997, 11, 425-445.
45. Teschner, M.; Henn, C.; Vollhardt, H.; Reiling, S.; Brickmann, J. Texture mapping: a new tool for molecular graphics. *J Mol Graph* 1994, 12, 98-105.
46. Sattler, M.; Liang, H.; Nettesheim, D.; Meadows, R. P.; Harlan, J. E.; Eberstadt, M.; Yoon, H. S.; Shuker, S. B.; Chang, B. S.; Minn, A. J.; Thompson, C. B.; Fesik, S. W. Structure of Bcl-xL-Bak peptide complex: recognition between regulators of apoptosis. *Science* (New York, N.Y.) 1997, 275, 983-986.
47. Ramjaun, A. R.; Tomlinson, S.; Eddaoudi, A.; Downward, J. Upregulation of two BH3-only proteins, Bmf and Bim, during TGF beta-induced apoptosis. *Oncogene* 2007, 26, 970-981.
48. Katsumata, M.; Siegel, R. M.; Louie, D. C.; Miyashita, T.; Tsujimoto, Y.; Nowell, P. C.; Greene, M. I.; Reed, J. C. Differential effects of Bcl-2 on T and B cells in transgenic mice. *Proc Natl Acad Sci USA* 1992, 89, 11376-11380.

Although the disclosure has been described with reference to the above examples, it will be understood that modifications and variations are encompassed within the spirit and scope of the disclosure. Accordingly, the disclosure is limited only by the following claims.

What is claimed is:
1. A compound of Formula I:

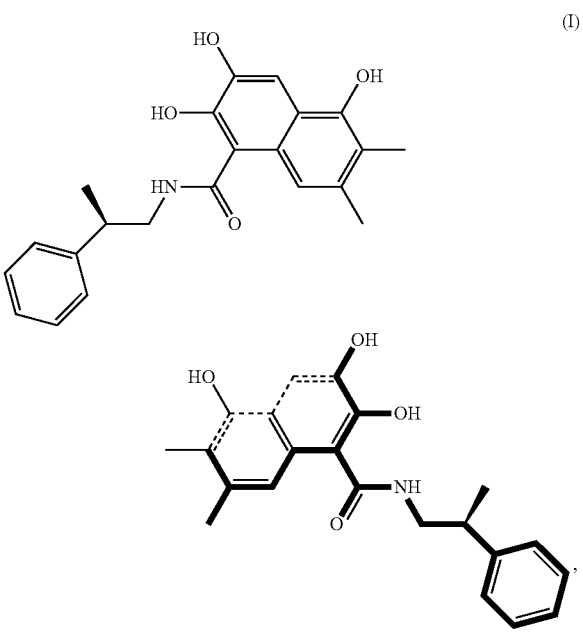

(I)

or a pharmaceutically acceptable salt thereof, specifically where both carbon chiral centers have the R configuration and the atropoisomer along the bi-naphthylene bond is (—).

2. A pharmaceutical composition, comprising the compound of Formula I of claim 1 and a pharmaceutically acceptable excipient.

3. A method for treating cancer, the method comprising the step of administering to a subject in need thereof a therapeutically effective amount of the compound of Formula I of claim 1, thereby treating the disease or the disorder and wherein the cancer is lung cancer, breast cancer, prostate cancer, renal cancer, hepatic cancer, pancreatic cancer, skin cancer, melanomas, leukemia, or lymphomas.

4. The method of claim 3, wherein the treatment includes inhibition of activity of at least one BCL-2 family protein.

5. The method of claim 3, further comprising administering the compound of Formula I in combination with an anti-cancer agent.

6. A method of treating cancer in a subject having at least one elevated BCL-2 family protein expression level, the method comprising the step of administering to the subject a therapeutically effective amount of the compound of Formula I of claim 1 and wherein the cancer is lung cancer, breast cancer, prostate cancer, renal cancer, hepatic cancer, pancreatic cancer, skin cancer, melanomas, leukemia, or lymphomas.

7. The method of claim 6, further comprising determining whether the subject is responsive to a therapy that utilizes the compound or composition, comprising determining the level of at least one of the BCL-2 family protein in the subject and comparing to a normal control sample, wherein an elevated level is indicative of a subject responsive to the therapy.

8. The method of claim 7, wherein the determination is made based on a sample from the subject.

9. A method of determining whether a subject is responsive to a therapy that utilizes of the compound of Formula I of claim 1, the method comprising the step of determining the level of at least one of the BCL-2 family protein in the subject having cancer and comparing to a normal control sample, wherein an elevated level is indicative of a subject responsive to the therapy and wherein the cancer is lung cancer, breast cancer, prostate cancer, renal cancer, hepatic cancer, pancreatic cancer, skin cancer, melanomas, leukemia, or lymphomas.

10. The method of claim 9, wherein the determination is made based on a sample from the subject.

11. The method of claim 9, wherein the sample is a biological fluid or tumor sample.

12. The method of claim 9, wherein the BCL-2 family polynucleotide or polypeptide is selected from BCL-2, BCL-XL, BCL-W, MCL-1, and BCL-Al.

13. A method of inducing apoptosis in a cancer cell having a level of at least one of the BCL-2 family protein member greater than levels in a control cell, the method comprising the step of administering to the cell an effective amount of the compound of Formula I of claim 1, to reduce the level of BCL-2 family protein(s) and induce apoptosis in the cell and wherein the cancer is lung cancer, breast cancer, prostate cancer, renal cancer, hepatic cancer, pancreatic cancer, skin cancer, melanomas, leukemia, or lymphomas.

14. A method of determining the effectiveness of a therapeutic regimen including administration of the compound of Formula I of claim 1, the method comprising the step of comparing the level of a BCL-2 family protein in a cell of the subject having cancer prior to and during treatment with the compound or composition, wherein a decreased level of BCL-2 family protein is indicative of effectiveness of the therapy that utilizes the compound or composition and wherein the cancer is lung cancer, breast cancer, prostate cancer, renal cancer, hepatic cancer, pancreatic cancer, skin cancer, melanomas, leukemia, or lymphomas.

15. A method of preparing the compound of Formula 1:

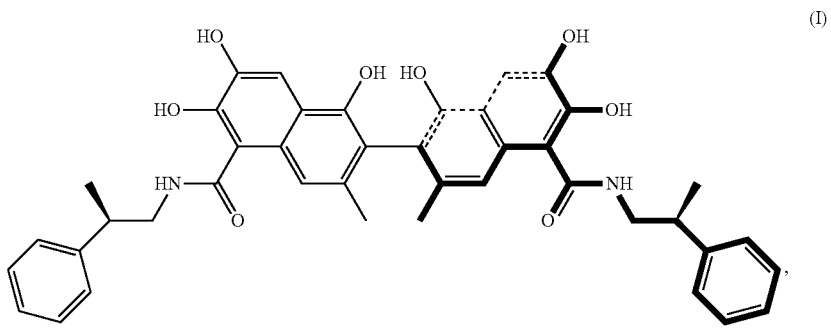

(I)

or a pharmaceutically salt thereof, the method comprising the steps of:

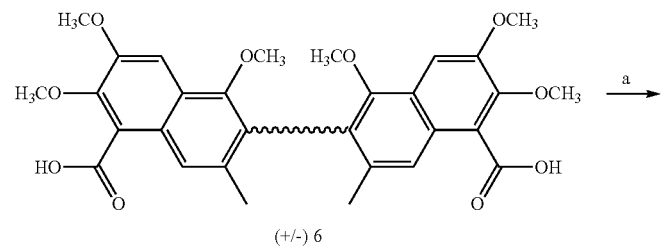

(+/-) 6

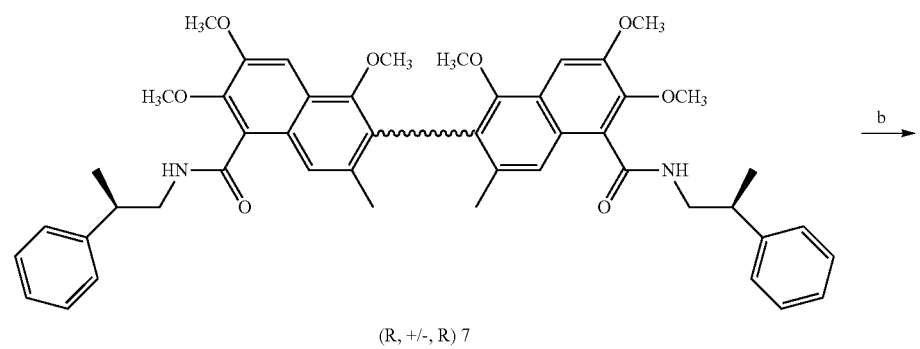

(R, +/-, R) 7

-continued

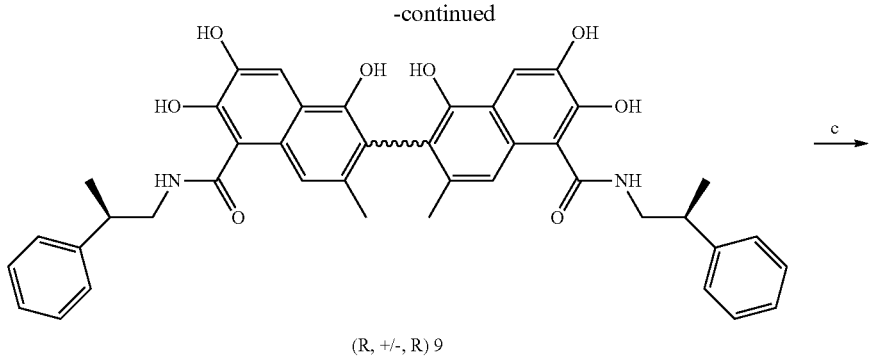

(R, +/−, R) 9

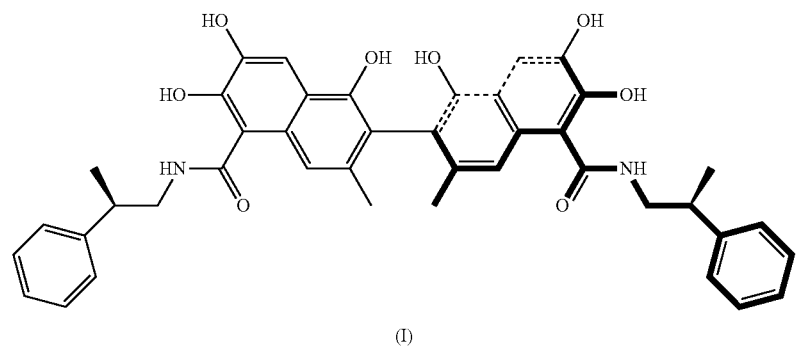

(I)

a) coupling the racemic carboxylic acid 6 with optically pure chiral amine (R)-(+)-β-methylphenethylamine in the presence of 1-ethyl-3-(3'-dimethylaminopropyl) carbodiimide (EDCI) to provide atropoisomer compound (R, +/−, R) 7;

b) demethylating atropoisomer compound (R, +/−, R) 7 with boron tribromide to provide atropisomer compound (R, +/−, R) 9; and c) resolving atropisomer compound (R, +/−, R) 9 using liquid chiral column chromatography to provide the compound of Formula I.

16. A method for isolating the atropisomers of the compound of Formula II:

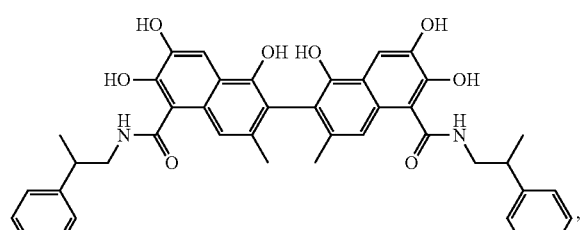

(II)

the method comprising the steps of:

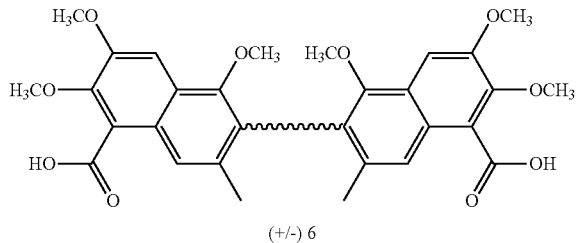

(+/−) 6

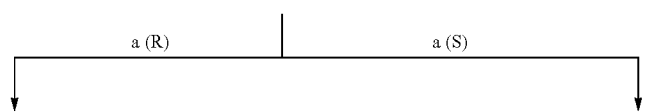

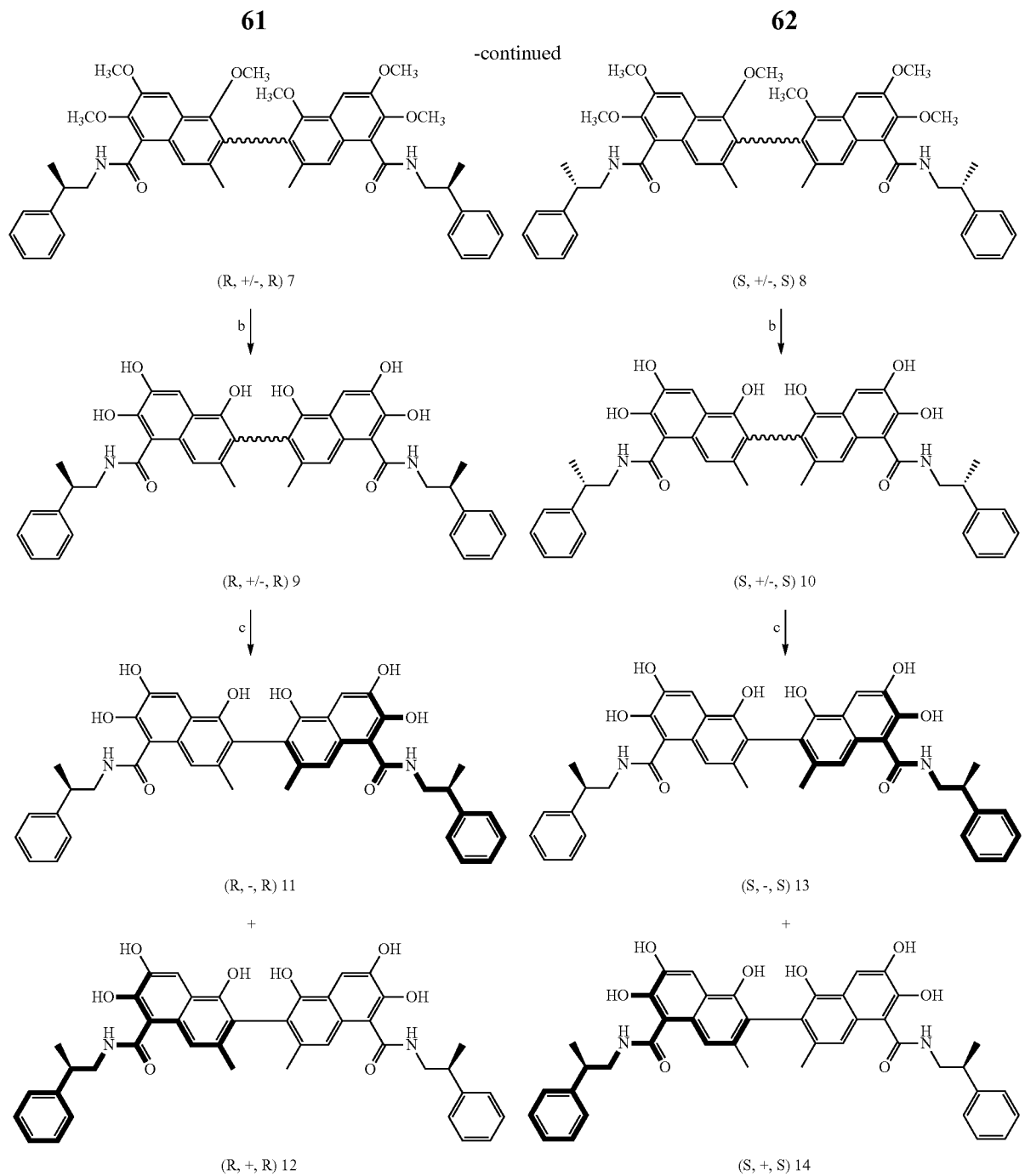

a) (R)) coupling the racemic carboxylic acid 6 with optically pure chiral amine (R)-(+)-β-methylphenethylamine in the presence of 1-ethyl-3-(3'-dimethylaminopropyl) carbodiimide (EDCI) to provide atropoisomer compound (R, +/−, R) 7, and a (S)) coupling the racemic carboxylic acid 6 with optically pure chiral amine (S)-(−)-β-methylphenethylamine in the presence of EDCI to provide atropoisomer compound (S, +/−, S) 8;

b) demethylating atropoisomer compound (R, +/−, R) 7 and atropoisomer compound (S, +/−, S) 8 with boron tribromide to provide atropisomer compound (R, +/−, R) 9 and atropisomer compound (S, +/−, S) 10, respectively; and c) resolving atropisomer compound (R, +/−, R) 9 and atropisomer compound (S, +/−, S) 10 using liquid chiral column chromatography to provide the atropisomers of the compound of Formula II, namely (R, −, R) 11, (R, +, R) 12, (S, −, S) 13, and (S, +, S) 14.

* * * * *